United States Patent
Fritzinger et al.

(10) Patent No.: US 9,433,407 B2
(45) Date of Patent: Sep. 6, 2016

(54) METHOD OF IMPLANTING A BONE FIXATION ASSEMBLY

(71) Applicant: Biomet Manufacturing, LLC, Warsaw, IN (US)

(72) Inventors: Daniel D. Fritzinger, Warsaw, IN (US); Nathan A. Winslow, Warsaw, IN (US); Robert Taylor, Granger, IN (US); Kevin T. Stone, Winona Lake, IN (US)

(73) Assignee: Biomet Manufacturing, LLC, Warsaw, IN (US)

( * ) Notice: Subject to any disclaimer, the term of this patent is extended or adjusted under 35 U.S.C. 154(b) by 0 days.

(21) Appl. No.: 14/989,414

(22) Filed: Jan. 6, 2016

(65) Prior Publication Data

US 2016/0113691 A1   Apr. 28, 2016

Related U.S. Application Data

(62) Division of application No. 13/342,646, filed on Jan. 3, 2012, now Pat. No. 9,259,217.

(51) Int. Cl.
*A61B 17/80* (2006.01)
*A61B 17/04* (2006.01)
*A61B 17/68* (2006.01)

(52) U.S. Cl.
CPC ......... *A61B 17/0401* (2013.01); *A61B 17/683* (2013.01); *A61B 17/8057* (2013.01); *A61B 17/8061* (2013.01); *A61B 2017/0404* (2013.01);
(Continued)

(58) Field of Classification Search
CPC .................. A61B 17/0401; A61B 2017/0404; A61B 17/80
See application file for complete search history.

(56) References Cited

U.S. PATENT DOCUMENTS

| 65,499 A | 6/1867 | Miller |
|---|---|---|
| 126,366 A | 4/1872 | Wills |

(Continued)

FOREIGN PATENT DOCUMENTS

| AU | 4957264 A | 3/1966 |
|---|---|---|
| AU | 440266 A1 | 10/1967 |

(Continued)

OTHER PUBLICATIONS

U.S. Appl. No. 13/342,646, Non Final Office Action mailed Mar. 4, 2015, 11 pgs.

(Continued)

*Primary Examiner* — Christian Sevilla
(74) *Attorney, Agent, or Firm* — Schwegman Lundberg & Woessner, P.A.

(57) ABSTRACT

A bone fixation assembly can include a suture button, a bone plate, and a suture assembly. The suture button can include a body that has a first end surface, a second end surface, and a circumferential outer surface. A first pair of passages can be formed through the body from the first end surface to the second end surface. The circumferential outer surface can include at least one protrusion or retaining rib extending radially therefrom. The bone plate defines an aperture. The suture button is configured to be at least partially received into the aperture in an assembled position such that the retaining rib engages the bone plate and inhibits withdrawal of the suture button from the aperture in the assembled position. The suture assembly includes a suture engaging member and a suture configured to couple the suture engaging member in the suture button.

20 Claims, 10 Drawing Sheets

(52) U.S. Cl.
CPC *A61B 2017/0414* (2013.01); *A61B 2017/0417* (2013.01); *A61B 2017/0437* (2013.01); *A61B 2017/0496* (2013.01)

(56) References Cited

U.S. PATENT DOCUMENTS

| | | | |
|---|---|---|---|
| 233,475 A | 10/1880 | Cook et al. | |
| 261,501 A | 7/1882 | Vandermark | |
| 268,407 A | 12/1882 | Hughes | |
| 401,677 A | 4/1889 | Autenrieth | |
| 417,805 A | 12/1889 | Beaman | |
| 487,304 A | 12/1892 | Todd | |
| 762,710 A | 6/1904 | Hall | |
| 837,767 A | 12/1906 | Aims | |
| 838,203 A | 12/1906 | Neil | |
| 1,059,631 A | 4/1913 | Popovics | |
| 1,131,155 A | 3/1915 | Murphy | |
| 1,153,450 A | 9/1915 | Schaff | |
| 1,346,940 A | 7/1920 | Collins | |
| 1,635,066 A | 7/1927 | Wells | |
| 1,950,799 A | 3/1934 | Jones | |
| 2,065,659 A | 12/1936 | Cullen | |
| 2,108,206 A | 2/1938 | Meeker | |
| 2,121,193 A | 6/1938 | Erich | |
| 2,242,003 A | 5/1941 | Lorenzo | |
| 2,267,925 A | 12/1941 | Johnston | |
| 2,302,986 A | 11/1942 | Vollrath | |
| 2,329,398 A | 9/1943 | Duffy | |
| RE22,857 E | 3/1947 | Ogburn | |
| 2,489,870 A | 11/1949 | William | |
| 2,526,959 A | 10/1950 | Lorenzo | |
| 2,528,456 A | 10/1950 | Thomas | |
| 2,562,419 A | 7/1951 | Ferris | |
| 2,581,564 A | 1/1952 | Jaime | |
| 2,600,395 A | 6/1952 | Joseph et al. | |
| 2,610,631 A | 9/1952 | Calicchio | |
| 2,665,597 A | 1/1954 | Hill | |
| 2,669,774 A | 2/1954 | Mitchell | |
| 2,698,986 A | 1/1955 | Brown | |
| 2,760,488 A | 8/1956 | Pierce | |
| 2,833,284 A | 5/1958 | Springer | |
| 2,846,712 A | 8/1958 | Moe | |
| 2,860,393 A | 11/1958 | Brock | |
| 2,880,728 A | 4/1959 | Rights | |
| 2,881,762 A | 4/1959 | Lowrie | |
| 2,883,096 A | 4/1959 | Horace | |
| 2,913,042 A | 11/1959 | John | |
| 3,000,009 A | 9/1961 | Selstad | |
| 3,003,155 A | 10/1961 | Mielzynski | |
| 3,013,559 A | 12/1961 | Thomas | |
| 3,037,619 A | 6/1962 | Ernest | |
| 3,039,460 A | 6/1962 | Chandler | |
| 3,090,386 A | 5/1963 | William | |
| 3,103,666 A | 9/1963 | Bone | |
| 3,123,077 A | 3/1964 | Alcamo | |
| 3,125,095 A | 3/1964 | Kaufman et al. | |
| 3,209,422 A | 10/1965 | Arthur | |
| 3,234,938 A | 2/1966 | Robinson | |
| 3,240,379 A | 3/1966 | Bremer et al. | |
| 3,250,271 A | 5/1966 | Jack | |
| 3,399,432 A | 9/1968 | Merser | |
| 3,409,014 A | 11/1968 | Grant | |
| RE26,501 E | 12/1968 | Himmelstein et al. | |
| 3,435,475 A | 4/1969 | Bisk | |
| 3,467,089 A | 9/1969 | Hasson | |
| 3,470,834 A | 10/1969 | Bone | |
| 3,470,875 A | 10/1969 | Johnson | |
| 3,500,820 A | 3/1970 | Almen | |
| 3,507,274 A | 4/1970 | Soichet | |
| 3,513,484 A | 5/1970 | Hausner | |
| 3,515,132 A | 6/1970 | Mcknight | |
| 3,522,803 A | 8/1970 | Majzlin | |
| 3,527,223 A | 9/1970 | Shein | |
| 3,533,406 A | 10/1970 | Tatum | |
| 3,541,591 A | 11/1970 | Hoegerman | |
| 3,547,389 A | 12/1970 | Mitchell | |
| 3,579,831 A | 5/1971 | Stevens et al. | |
| 3,590,616 A | 7/1971 | Schussler | |
| 3,608,095 A | 9/1971 | Barry | |
| 3,618,447 A | 11/1971 | Goins | |
| 3,628,530 A | 12/1971 | Schwartz | |
| 3,643,649 A | 2/1972 | Amato | |
| 3,648,705 A | 3/1972 | Lary | |
| 3,656,483 A | 4/1972 | Rudel | |
| 3,659,597 A | 5/1972 | Wolfers | |
| 3,664,345 A | 5/1972 | Dabbs et al. | |
| 3,665,560 A | 5/1972 | Bennett et al. | |
| 3,675,639 A | 7/1972 | Cimber | |
| 3,683,422 A | 8/1972 | Stemmer et al. | |
| 3,692,022 A | 9/1972 | Ewing | |
| 3,695,271 A | 10/1972 | Chodorow | |
| 3,699,969 A | 10/1972 | Allen | |
| 3,716,058 A | 2/1973 | Tanner | |
| 3,744,488 A | 7/1973 | Cox | |
| 3,752,516 A | 8/1973 | Mumma | |
| 3,757,629 A | 9/1973 | Schneider | |
| 3,763,856 A | 10/1973 | Blomberg | |
| 3,771,520 A | 11/1973 | Lerner | |
| 3,777,748 A | 12/1973 | Abramson | |
| 3,807,407 A | 4/1974 | Schweizer | |
| 3,810,456 A | 5/1974 | Karman | |
| 3,825,010 A | 7/1974 | McDonald | |
| 3,840,017 A | 10/1974 | Violante | |
| 3,842,824 A | 10/1974 | Neufeld | |
| 3,842,840 A | 10/1974 | Schweizer | |
| 3,845,772 A | 11/1974 | Smith | |
| 3,867,933 A | 2/1975 | Kitrilakis | |
| 3,867,944 A | 2/1975 | Samuels | |
| 3,871,368 A | 3/1975 | Johnson et al. | |
| 3,871,379 A | 3/1975 | Clarke | |
| 3,874,388 A | 4/1975 | King et al. | |
| 3,875,648 A | 4/1975 | Bone | |
| 3,877,570 A | 4/1975 | Barry | |
| 3,880,156 A | 4/1975 | Hoff | |
| 3,881,475 A | 5/1975 | Gordon et al. | |
| 3,889,666 A | 6/1975 | Lerner | |
| 3,892,240 A | 7/1975 | Park | |
| 3,896,500 A | 7/1975 | Rambert et al. | |
| 3,907,442 A | 9/1975 | Reid | |
| 3,910,281 A | 10/1975 | Kletschka | |
| 3,918,444 A | 11/1975 | Hoff et al. | |
| 3,918,455 A | 11/1975 | Coplan | |
| 3,927,666 A | 12/1975 | Hoff | |
| 3,931,667 A | 1/1976 | Merser et al. | |
| 3,933,153 A | 1/1976 | Csatary et al. | |
| 3,937,217 A | 2/1976 | Kosonen | |
| 3,943,932 A | 3/1976 | Woo | |
| 3,946,728 A | 3/1976 | Bettex | |
| 3,946,740 A | 3/1976 | Bassett | |
| 3,953,896 A | 5/1976 | Treace | |
| 3,954,103 A | 5/1976 | Garcia-roel et al. | |
| 3,961,632 A | 6/1976 | Moossun | |
| 3,973,560 A | 8/1976 | Emmett | |
| 3,976,079 A | 8/1976 | Samuels et al. | |
| 3,977,050 A | 8/1976 | Perez | |
| 3,979,799 A | 9/1976 | Merser et al. | |
| 3,985,138 A | 10/1976 | Jarvik | |
| 3,990,619 A | 11/1976 | Russell | |
| 4,005,707 A | 2/1977 | Moulding, Jr. | |
| 4,006,747 A | 2/1977 | Kronenthal et al. | |
| 4,007,743 A | 2/1977 | Blake | |
| 4,013,071 A | 3/1977 | Rosenberg | |
| 4,026,281 A | 5/1977 | Mayberry et al. | |
| 4,050,100 A | 9/1977 | Barry | |
| 4,054,954 A | 10/1977 | Nakayama et al. | |
| 4,085,466 A | 4/1978 | Goodfellow et al. | |
| 4,094,313 A | 6/1978 | Komamura et al. | |
| 4,103,690 A | 8/1978 | Harris | |
| RE29,819 E | 10/1978 | Bone | |
| 4,121,487 A | 10/1978 | Bone | |
| 4,143,656 A | 3/1979 | Holmes | |
| 4,144,876 A | 3/1979 | Deleo | |
| 4,149,277 A | 4/1979 | Bokros | |
| 4,157,714 A | 6/1979 | Foltz et al. | |

(56) References Cited

U.S. PATENT DOCUMENTS

| | | |
|---|---|---|
| 4,160,453 A | 7/1979 | Miller |
| 4,164,225 A | 8/1979 | Johnson et al. |
| 4,172,458 A | 10/1979 | Pereyra |
| 4,175,555 A | 11/1979 | Herbert |
| 4,185,636 A | 1/1980 | Gabbay et al. |
| 4,196,883 A | 4/1980 | Einhorn et al. |
| 4,210,148 A | 7/1980 | Stivala |
| 4,235,161 A | 11/1980 | Kunreuther |
| 4,235,238 A | 11/1980 | Ogiu et al. |
| 4,237,779 A | 12/1980 | Kunreuther |
| 4,243,037 A | 1/1981 | Smith |
| 4,249,525 A | 2/1981 | Krzeminski |
| 4,263,913 A | 4/1981 | Malmin |
| 4,265,246 A | 5/1981 | Barry |
| 4,273,117 A | 6/1981 | Neuhauser |
| 4,275,717 A | 6/1981 | Bolesky |
| 4,287,807 A | 9/1981 | Pacharis et al. |
| 4,291,698 A | 9/1981 | Fuchs et al. |
| 4,301,551 A | 11/1981 | Dore et al. |
| 4,312,337 A | 1/1982 | Donohue |
| 4,316,469 A | 2/1982 | Kapitanov |
| 4,326,531 A | 4/1982 | Shimonaka |
| 4,345,601 A | 8/1982 | Fukuda |
| 4,349,027 A | 9/1982 | Difrancesco |
| 4,388,921 A | 6/1983 | Sutter et al. |
| 4,400,833 A | 8/1983 | Kurland |
| 4,402,445 A | 9/1983 | Green |
| 4,409,974 A | 10/1983 | Freedland et al. |
| 4,438,769 A | 3/1984 | Pratt et al. |
| 4,441,489 A | 4/1984 | Evans et al. |
| 4,454,875 A | 6/1984 | Pratt et al. |
| 4,462,395 A | 7/1984 | Johnson |
| 4,463,753 A | 8/1984 | Gustilo |
| 4,473,102 A | 9/1984 | Ohman et al. |
| 4,484,570 A | 11/1984 | Sutter et al. |
| 4,489,446 A | 12/1984 | Reed |
| 4,493,323 A | 1/1985 | Albright et al. |
| 4,496,468 A | 1/1985 | House et al. |
| 4,505,274 A | 3/1985 | Speelman |
| 4,509,516 A | 4/1985 | Richmond |
| 4,531,522 A | 7/1985 | Bedi et al. |
| 4,532,926 A | 8/1985 | O'holla |
| 4,534,350 A | 8/1985 | Golden et al. |
| 4,535,764 A | 8/1985 | Ebert |
| 4,537,185 A | 8/1985 | Stednitz |
| 4,549,545 A | 10/1985 | Levy |
| 4,549,652 A | 10/1985 | Free |
| 4,561,432 A | 12/1985 | Mazor |
| 4,564,007 A | 1/1986 | Coombs |
| 4,570,623 A | 2/1986 | Ellison et al. |
| 4,573,844 A | 3/1986 | Smith |
| 4,576,608 A | 3/1986 | Homsy |
| 4,584,722 A | 4/1986 | Levy et al. |
| 4,590,928 A | 5/1986 | Hunt et al. |
| 4,595,007 A | 6/1986 | Mericle |
| 4,596,249 A | 6/1986 | Freda et al. |
| 4,602,635 A | 7/1986 | Mulhollan et al. |
| 4,602,636 A | 7/1986 | Noiles |
| 4,604,997 A | 8/1986 | De et al. |
| 4,605,414 A | 8/1986 | Czajka |
| 4,616,650 A | 10/1986 | Green et al. |
| 4,621,640 A | 11/1986 | Mulhollan et al. |
| 4,624,254 A | 11/1986 | Mcgarry et al. |
| 4,632,100 A | 12/1986 | Somers et al. |
| 4,635,637 A | 1/1987 | Schreiber |
| 4,636,121 A | 1/1987 | Miller |
| 4,641,652 A | 2/1987 | Hutterer et al. |
| 4,649,952 A | 3/1987 | Jobe |
| 4,653,486 A | 3/1987 | Coker |
| 4,653,487 A | 3/1987 | Maale |
| 4,653,489 A | 3/1987 | Tronzo |
| 4,655,777 A | 4/1987 | Dunn |
| 4,662,068 A | 5/1987 | Polonsky |
| 4,667,662 A | 5/1987 | Titone et al. |
| 4,667,675 A | 5/1987 | Davis |
| 4,669,473 A | 6/1987 | Richards et al. |
| 4,683,895 A | 8/1987 | Pohndorf |
| 4,688,561 A | 8/1987 | Reese |
| 4,690,169 A | 9/1987 | Jobe |
| 4,705,040 A | 11/1987 | Mueller et al. |
| 4,708,132 A | 11/1987 | Silvestrini |
| 4,716,893 A | 1/1988 | Fischer et al. |
| 4,719,671 A | 1/1988 | Ito et al. |
| 4,719,917 A | 1/1988 | Barrows et al. |
| 4,723,540 A | 2/1988 | Gilmer, Jr. |
| 4,724,839 A | 2/1988 | Bedi et al. |
| 4,728,332 A | 3/1988 | Albrektsson |
| 4,738,255 A | 4/1988 | Goble et al. |
| 4,741,330 A | 5/1988 | Hayhurst |
| 4,741,336 A | 5/1988 | Failla et al. |
| 4,744,353 A | 5/1988 | Mcfarland |
| 4,744,793 A | 5/1988 | Parr et al. |
| 4,750,492 A | 6/1988 | Jacobs |
| 4,760,843 A | 8/1988 | Fischer et al. |
| 4,760,844 A | 8/1988 | Kyle |
| 4,760,848 A | 8/1988 | Hasson |
| 4,772,261 A | 9/1988 | Von Hoff et al. |
| 4,772,286 A | 9/1988 | Goble et al. |
| 4,773,910 A | 9/1988 | Chen et al. |
| 4,775,380 A | 10/1988 | Seedhom et al. |
| 4,776,328 A | 10/1988 | Frey et al. |
| 4,781,190 A | 11/1988 | Lee |
| 4,784,126 A | 11/1988 | Hourahane |
| 4,787,882 A | 11/1988 | Claren |
| 4,790,297 A | 12/1988 | Luque |
| 4,793,363 A | 12/1988 | Ausherman et al. |
| 4,809,695 A | 3/1989 | Gwathmey et al. |
| 4,813,406 A | 3/1989 | Ogle, II |
| 4,823,794 A | 4/1989 | Pierce |
| 4,828,562 A | 5/1989 | Kenna |
| 4,832,026 A | 5/1989 | Jones |
| 4,834,098 A | 5/1989 | Jones |
| 4,838,282 A | 6/1989 | Strasser et al. |
| 4,841,960 A | 6/1989 | Garner |
| 4,851,005 A | 7/1989 | Hunt et al. |
| 4,858,608 A | 8/1989 | Mcquilkin |
| 4,860,513 A | 8/1989 | Whitman |
| 4,863,383 A | 9/1989 | Grafelmann |
| 4,870,957 A | 10/1989 | Goble et al. |
| 4,873,976 A | 10/1989 | Schreiber |
| 4,887,601 A | 12/1989 | Richards |
| 4,890,615 A | 1/1990 | Caspari et al. |
| 4,893,619 A | 1/1990 | Dale et al. |
| 4,893,974 A | 1/1990 | Fischer et al. |
| 4,895,148 A | 1/1990 | Bays et al. |
| 4,896,668 A | 1/1990 | Popoff et al. |
| 4,898,156 A | 2/1990 | Gatturna et al. |
| 4,899,743 A | 2/1990 | Nicholson et al. |
| 4,901,721 A | 2/1990 | Hakki |
| 4,923,461 A | 5/1990 | Caspari et al. |
| 4,927,421 A | 5/1990 | Goble et al. |
| 4,946,468 A | 8/1990 | Li |
| 4,950,270 A | 8/1990 | Bowman et al. |
| 4,950,285 A | 8/1990 | Wilk |
| 4,960,381 A | 10/1990 | Niznick |
| 4,961,741 A | 10/1990 | Hayhurst |
| 4,968,315 A | 11/1990 | Gatturna |
| 4,968,317 A | 11/1990 | Tormala et al. |
| 4,969,886 A | 11/1990 | Cziffer et al. |
| 4,976,736 A | 12/1990 | White et al. |
| 4,978,350 A | 12/1990 | Wagenknecht |
| 4,979,956 A | 12/1990 | Silvestrini |
| 4,983,176 A | 1/1991 | Cushman et al. |
| 4,988,351 A | 1/1991 | Paulos et al. |
| 4,994,074 A | 2/1991 | Bezwada et al. |
| 4,997,433 A | 3/1991 | Goble et al. |
| 5,002,550 A | 3/1991 | Li |
| 5,002,562 A | 3/1991 | Oberlander |
| 5,007,921 A | 4/1991 | Brown |
| 5,030,224 A | 7/1991 | Wright |
| 5,037,422 A | 8/1991 | Hayhurst et al. |
| 5,041,129 A | 8/1991 | Hayhurst et al. |
| 5,046,513 A | 9/1991 | Gatturna et al. |
| 5,047,030 A | 9/1991 | Draenert |

(56) References Cited

U.S. PATENT DOCUMENTS

| | | |
|---|---|---|
| 5,053,046 A | 10/1991 | Janese |
| 5,053,047 A | 10/1991 | Yoon |
| 5,059,201 A | 10/1991 | Asnis |
| 5,059,206 A | 10/1991 | Winters |
| 5,061,277 A | 10/1991 | Carpentier et al. |
| 5,062,344 A | 11/1991 | Gerker |
| 5,062,843 A | 11/1991 | Mahony, III |
| 5,074,874 A | 12/1991 | Yoon et al. |
| 5,078,731 A | 1/1992 | Hayhurst |
| 5,078,843 A | 1/1992 | Pratt |
| 5,084,050 A | 1/1992 | Draenert |
| 5,084,058 A | 1/1992 | Li |
| 5,085,661 A | 2/1992 | Moss |
| 5,087,263 A | 2/1992 | Li |
| 5,092,866 A | 3/1992 | Breard et al. |
| 5,098,433 A | 3/1992 | Freedland |
| 5,098,435 A | 3/1992 | Stednitz et al. |
| 5,100,415 A | 3/1992 | Hayhurst |
| 5,100,417 A | 3/1992 | Cerier |
| 5,116,337 A | 5/1992 | Johnson |
| 5,116,373 A | 5/1992 | Jakob et al. |
| 5,116,375 A | 5/1992 | Hofmann |
| 5,123,913 A | 6/1992 | Wilk et al. |
| 5,123,914 A | 6/1992 | Cope |
| 5,127,785 A | 7/1992 | Faucher |
| 5,129,901 A | 7/1992 | Decoste |
| 5,129,902 A | 7/1992 | Goble et al. |
| 5,129,904 A | 7/1992 | Illi |
| 5,129,906 A | 7/1992 | Ross et al. |
| 5,139,499 A | 8/1992 | Small et al. |
| 5,139,520 A | 8/1992 | Rosenberg |
| 5,143,498 A | 9/1992 | Whitman |
| 5,147,362 A | 9/1992 | Goble |
| 5,149,329 A | 9/1992 | Richardson |
| 5,152,790 A | 10/1992 | Rosenberg et al. |
| 5,154,189 A | 10/1992 | Oberlander |
| 5,156,616 A | 10/1992 | Meadows et al. |
| 5,163,960 A | 11/1992 | Bonutti |
| D331,626 S | 12/1992 | Hayhurst et al. |
| 5,169,400 A | 12/1992 | Muhling et al. |
| 5,176,682 A | 1/1993 | Chow |
| 5,178,629 A | 1/1993 | Kammerer |
| 5,183,458 A | 2/1993 | Marx |
| 5,192,282 A | 3/1993 | Draenert |
| 5,197,987 A | 3/1993 | Koch et al. |
| 5,203,784 A | 4/1993 | Ross et al. |
| 5,203,787 A | 4/1993 | Noblitt et al. |
| 5,207,679 A | 5/1993 | Li |
| 5,209,753 A | 5/1993 | Biedermann et al. |
| 5,209,805 A | 5/1993 | Spraggins |
| 5,211,647 A | 5/1993 | Schmieding |
| 5,211,650 A | 5/1993 | Noda |
| 5,214,987 A | 6/1993 | Fenton, Sr. |
| 5,219,359 A | 6/1993 | McQuilkin et al. |
| 5,222,976 A | 6/1993 | Yoon |
| 5,224,946 A | 7/1993 | Hayhurst et al. |
| 5,230,699 A | 7/1993 | Grasinger |
| 5,232,436 A | 8/1993 | Janevski |
| 5,234,435 A | 8/1993 | Seagrave, Jr. |
| 5,235,238 A | 8/1993 | Nomura et al. |
| 5,236,445 A | 8/1993 | Hayhurst et al. |
| 5,236,461 A | 8/1993 | Forte |
| 5,242,447 A | 9/1993 | Borzone |
| 5,246,441 A | 9/1993 | Ross et al. |
| 5,249,899 A | 10/1993 | Wilson |
| 5,258,015 A | 11/1993 | Li et al. |
| 5,258,016 A | 11/1993 | Dipoto et al. |
| 5,258,040 A | 11/1993 | Bruchman et al. |
| 5,268,001 A | 12/1993 | Nicholson et al. |
| 5,269,160 A | 12/1993 | Wood |
| 5,269,783 A | 12/1993 | Sander |
| 5,269,809 A | 12/1993 | Hayhurst et al. |
| 5,281,422 A | 1/1994 | Badylak et al. |
| 5,282,809 A | 2/1994 | Kammerer et al. |
| 5,282,832 A | 2/1994 | Toso et al. |
| 5,285,040 A | 2/1994 | Brandberg et al. |
| 5,290,217 A | 3/1994 | Campos |
| 5,306,301 A | 4/1994 | Graf et al. |
| 5,312,422 A | 5/1994 | Trott |
| 5,312,438 A | 5/1994 | Johnson |
| 5,318,577 A | 6/1994 | Li |
| 5,318,578 A | 6/1994 | Hasson |
| 5,320,115 A | 6/1994 | Kenna |
| 5,320,626 A | 6/1994 | Schmieding |
| 5,320,633 A | 6/1994 | Allen et al. |
| 5,324,308 A | 6/1994 | Pierce |
| 5,334,204 A | 8/1994 | Clewett et al. |
| 5,336,229 A | 8/1994 | Noda |
| 5,336,231 A | 8/1994 | Adair |
| 5,336,240 A | 8/1994 | Metzler et al. |
| 5,342,369 A | 8/1994 | Harryman, II |
| 5,346,462 A | 9/1994 | Barber |
| 5,354,298 A | 10/1994 | Lee et al. |
| 5,356,413 A | 10/1994 | Martins et al. |
| 5,358,511 A | 10/1994 | Gatturna et al. |
| 5,360,431 A | 11/1994 | Puno et al. |
| 5,362,294 A | 11/1994 | Seitzinger |
| 5,364,400 A | 11/1994 | Rego, Jr. et al. |
| 5,368,599 A | 11/1994 | Hirsch et al. |
| 5,370,661 A | 12/1994 | Branch |
| 5,370,662 A | 12/1994 | Stone et al. |
| 5,372,146 A | 12/1994 | Branch |
| 5,372,604 A | 12/1994 | Trott |
| 5,372,821 A | 12/1994 | Badylak et al. |
| 5,374,268 A | 12/1994 | Sander |
| 5,379,492 A | 1/1995 | Glesser |
| 5,383,878 A | 1/1995 | Roger et al. |
| 5,383,904 A | 1/1995 | Totakura et al. |
| 5,391,171 A | 2/1995 | Schmieding |
| 5,391,176 A | 2/1995 | De La |
| 5,393,302 A | 2/1995 | Clark et al. |
| RE34,871 E | 3/1995 | Mcguire et al. |
| 5,397,356 A | 3/1995 | Goble et al. |
| 5,403,328 A | 4/1995 | Shallman |
| 5,403,329 A | 4/1995 | Hinchcliffe |
| 5,403,348 A | 4/1995 | Bonutti |
| 5,417,691 A | 5/1995 | Hayhurst |
| 5,417,712 A | 5/1995 | Whittaker et al. |
| 5,423,819 A | 6/1995 | Small et al. |
| 5,423,823 A | 6/1995 | Schmieding |
| 5,423,860 A | 6/1995 | Lizardi et al. |
| 5,425,733 A | 6/1995 | Schmieding |
| 5,425,766 A | 6/1995 | Bowald |
| 5,433,751 A | 7/1995 | Christel et al. |
| 5,437,680 A | 8/1995 | Yoon |
| 5,439,684 A | 8/1995 | Prewett et al. |
| 5,443,468 A | 8/1995 | Johnson |
| 5,443,482 A | 8/1995 | Stone et al. |
| 5,443,483 A | 8/1995 | Kirsch |
| 5,443,509 A | 8/1995 | Boucher et al. |
| 5,445,833 A | 8/1995 | Badylak et al. |
| 5,447,512 A | 9/1995 | Wilson et al. |
| 5,451,203 A | 9/1995 | Lamb |
| 5,454,811 A | 10/1995 | Huebner |
| 5,456,685 A | 10/1995 | Huebner |
| 5,456,722 A | 10/1995 | Mcleod et al. |
| 5,458,601 A | 10/1995 | Young, Jr. et al. |
| 5,458,604 A | 10/1995 | Schmieding |
| 5,462,560 A | 10/1995 | Stevens |
| 5,464,426 A | 11/1995 | Bonutti |
| 5,464,427 A | 11/1995 | Curtis et al. |
| 5,464,440 A | 11/1995 | Johansson |
| 5,466,237 A | 11/1995 | Byrd, III et al. |
| 5,467,786 A | 11/1995 | Allen et al. |
| 5,470,334 A | 11/1995 | Ross et al. |
| 5,470,337 A | 11/1995 | Moss |
| 5,470,338 A | 11/1995 | Whitfield et al. |
| 5,472,452 A | 12/1995 | Trott |
| 5,474,565 A | 12/1995 | Trott |
| 5,474,568 A | 12/1995 | Scott |
| 5,474,572 A | 12/1995 | Hayhurst |
| 5,478,344 A | 12/1995 | Stone et al. |
| 5,478,345 A | 12/1995 | Stone et al. |
| 5,480,403 A | 1/1996 | Lee et al. |

(56) References Cited

U.S. PATENT DOCUMENTS

| | | |
|---|---|---|
| 5,480,406 A | 1/1996 | Nolan et al. |
| 5,484,442 A | 1/1996 | Melker et al. |
| 5,486,197 A | 1/1996 | Le et al. |
| 5,490,750 A | 2/1996 | Gundy |
| 5,496,331 A | 3/1996 | Xu et al. |
| 5,496,348 A | 3/1996 | Bonutti |
| 5,500,000 A | 3/1996 | Feagin et al. |
| 5,505,736 A | 4/1996 | Reimels et al. |
| 5,507,754 A | 4/1996 | Green et al. |
| 5,520,691 A | 5/1996 | Branch |
| 5,520,702 A | 5/1996 | Sauer et al. |
| 5,522,817 A | 6/1996 | Sander et al. |
| 5,522,820 A | 6/1996 | Caspari et al. |
| 5,522,844 A | 6/1996 | Johnson |
| 5,522,845 A | 6/1996 | Wenstrom, Jr. |
| 5,522,846 A | 6/1996 | Bonutti |
| 5,524,946 A | 6/1996 | Thompson |
| 5,527,321 A | 6/1996 | Hinchliffe |
| 5,527,342 A | 6/1996 | Pietrzak et al. |
| 5,527,343 A | 6/1996 | Bonutti |
| 5,534,012 A | 7/1996 | Bonutti |
| 5,540,718 A | 7/1996 | Bartlett |
| 5,545,178 A | 8/1996 | Kensey et al. |
| 5,545,228 A | 8/1996 | Kambin |
| 5,549,613 A | 8/1996 | Goble et al. |
| 5,549,617 A | 8/1996 | Green et al. |
| 5,549,630 A | 8/1996 | Bonutti |
| 5,549,631 A | 8/1996 | Bonutti |
| 5,562,683 A | 10/1996 | Chan |
| 5,562,685 A | 10/1996 | Mollenauer et al. |
| 5,562,686 A | 10/1996 | Sauer et al. |
| 5,569,269 A | 10/1996 | Hart et al. |
| 5,569,305 A | 10/1996 | Bonutti |
| 5,571,090 A | 11/1996 | Sherts |
| 5,571,139 A | 11/1996 | Jenkins, Jr. |
| 5,572,655 A | 11/1996 | Tuljapurkar et al. |
| 5,573,286 A | 11/1996 | Rogozinski |
| 5,573,542 A | 11/1996 | Stevens |
| 5,573,548 A | 11/1996 | Nazre et al. |
| 5,577,299 A | 11/1996 | Thompson et al. |
| 5,578,057 A | 11/1996 | Wenstrom, Jr. |
| 5,584,695 A | 12/1996 | Sachdeva et al. |
| 5,584,835 A | 12/1996 | Greenfield |
| 5,584,836 A | 12/1996 | Ballintyn et al. |
| 5,584,862 A | 12/1996 | Bonutti |
| 5,586,986 A | 12/1996 | Hinchliffe |
| 5,588,575 A | 12/1996 | Davignon |
| 5,591,180 A | 1/1997 | Hinchliffe |
| 5,591,181 A | 1/1997 | Stone et al. |
| 5,591,207 A | 1/1997 | Coleman |
| 5,593,407 A | 1/1997 | Reis |
| 5,593,425 A | 1/1997 | Bonutti et al. |
| 5,601,557 A | 2/1997 | Hayhurst |
| 5,601,559 A | 2/1997 | Melker et al. |
| 5,601,571 A | 2/1997 | Moss |
| 5,603,716 A | 2/1997 | Morgan et al. |
| 5,607,429 A | 3/1997 | Hayano et al. |
| 5,618,290 A | 4/1997 | Toy et al. |
| 5,628,756 A | 5/1997 | Barker, Jr. et al. |
| 5,628,766 A | 5/1997 | Johnson |
| 5,630,824 A | 5/1997 | Hart |
| 5,632,748 A | 5/1997 | Beck, Jr. et al. |
| 5,641,256 A | 6/1997 | Gundy |
| 5,643,266 A | 7/1997 | Li |
| 5,643,269 A | 7/1997 | Harle |
| 5,643,295 A | 7/1997 | Yoon |
| 5,643,320 A | 7/1997 | Lower et al. |
| 5,643,321 A | 7/1997 | Mcdevitt |
| 5,645,546 A | 7/1997 | Fard |
| 5,645,547 A | 7/1997 | Coleman |
| 5,645,568 A | 7/1997 | Chervitz et al. |
| 5,645,588 A | 7/1997 | Graf et al. |
| 5,647,874 A | 7/1997 | Hayhurst |
| 5,649,963 A | 7/1997 | Mcdevitt |
| 5,658,289 A | 8/1997 | Boucher et al. |
| 5,658,299 A | 8/1997 | Hart |
| 5,658,313 A | 8/1997 | Thal |
| 5,662,658 A | 9/1997 | Wenstrom, Jr. |
| 5,662,663 A | 9/1997 | Shallman |
| 5,665,112 A | 9/1997 | Thal |
| 5,667,513 A | 9/1997 | Torrie et al. |
| 5,671,695 A | 9/1997 | Schroeder |
| 5,674,224 A | 10/1997 | Howell et al. |
| 5,679,723 A | 10/1997 | Cooper |
| 5,681,352 A | 10/1997 | Clancy, III et al. |
| 5,683,419 A | 11/1997 | Thal |
| 5,688,285 A | 11/1997 | Yamada |
| 5,690,676 A | 11/1997 | Dipoto et al. |
| 5,690,678 A | 11/1997 | Johnson |
| 5,695,497 A | 12/1997 | Stahelin |
| 5,697,929 A | 12/1997 | Mellinger |
| 5,699,657 A | 12/1997 | Paulson |
| 5,702,397 A | 12/1997 | Goble et al. |
| 5,702,422 A | 12/1997 | Stone |
| 5,702,462 A | 12/1997 | Oberlander |
| 5,707,373 A | 1/1998 | Sevrain et al. |
| 5,713,005 A | 1/1998 | Proebsting |
| 5,713,904 A | 2/1998 | Errico et al. |
| 5,713,905 A | 2/1998 | Goble et al. |
| 5,713,921 A | 2/1998 | Bonutti |
| 5,716,359 A | 2/1998 | Ojima et al. |
| 5,716,397 A | 2/1998 | Myers |
| 5,718,717 A | 2/1998 | Bonutti |
| 5,720,747 A | 2/1998 | Burke |
| 5,720,765 A | 2/1998 | Thal |
| 5,720,766 A | 2/1998 | Zang et al. |
| 5,725,549 A | 3/1998 | Lam |
| 5,725,556 A | 3/1998 | Moser et al. |
| 5,725,581 A | 3/1998 | Branemark |
| 5,725,582 A | 3/1998 | Bevan et al. |
| 5,726,722 A | 3/1998 | Uehara et al. |
| 5,728,107 A | 3/1998 | Zlock et al. |
| 5,728,109 A | 3/1998 | Schulze et al. |
| 5,728,136 A | 3/1998 | Thal |
| 5,733,293 A | 3/1998 | Scirica et al. |
| 5,733,306 A | 3/1998 | Bonutti |
| 5,733,307 A | 3/1998 | Dinsdale |
| 5,735,875 A | 4/1998 | Bonutti et al. |
| 5,741,259 A | 4/1998 | Chan |
| 5,741,281 A | 4/1998 | Martin |
| 5,743,912 A | 4/1998 | Lahille et al. |
| 5,746,751 A | 5/1998 | Sherts |
| 5,746,752 A | 5/1998 | Burkhart |
| 5,746,754 A | 5/1998 | Chan |
| 5,749,898 A | 5/1998 | Schulze et al. |
| 5,755,729 A | 5/1998 | De La et al. |
| 5,766,176 A | 6/1998 | Duncan |
| 5,766,250 A | 6/1998 | Chervitz et al. |
| 5,769,894 A | 6/1998 | Ferragamo |
| 5,769,899 A | 6/1998 | Schwartz et al. |
| 5,772,673 A | 6/1998 | Cuny et al. |
| 5,776,196 A | 7/1998 | Matsuzaki et al. |
| 5,782,862 A | 7/1998 | Bonutti |
| 5,782,864 A | 7/1998 | Lizardi |
| 5,782,866 A | 7/1998 | Wenstrom, Jr. |
| 5,785,714 A | 7/1998 | Morgan et al. |
| 5,792,142 A | 8/1998 | Galitzer |
| 5,792,149 A | 8/1998 | Sherts et al. |
| 5,796,127 A | 8/1998 | Hayafuji et al. |
| 5,797,928 A | 8/1998 | Kogasaka |
| 5,800,407 A | 9/1998 | Eldor |
| 5,810,824 A | 9/1998 | Chan |
| 5,810,848 A | 9/1998 | Hayhurst |
| 5,814,069 A | 9/1998 | Schulze et al. |
| 5,814,070 A | 9/1998 | Borzone et al. |
| 5,814,072 A | 9/1998 | Bonutti |
| 5,814,073 A | 9/1998 | Bonutti |
| 5,823,980 A | 10/1998 | Kopfer |
| 5,824,011 A | 10/1998 | Stone et al. |
| 5,843,084 A | 12/1998 | Hart et al. |
| 5,845,645 A | 12/1998 | Bonutti |
| 5,846,254 A | 12/1998 | Schulze et al. |
| 5,848,983 A | 12/1998 | Basaj et al. |
| 5,860,973 A | 1/1999 | Michelson |

(56) References Cited

U.S. PATENT DOCUMENTS

| | | |
|---|---|---|
| 5,868,740 A | 2/1999 | LeVeen et al. |
| 5,868,789 A | 2/1999 | Huebner |
| 5,871,484 A | 2/1999 | Spievack et al. |
| 5,871,486 A | 2/1999 | Huebner |
| 5,871,490 A | 2/1999 | Schulze et al. |
| 5,885,294 A | 3/1999 | Pedlick et al. |
| 5,891,168 A | 4/1999 | Thal |
| 5,893,592 A | 4/1999 | Schulze et al. |
| 5,895,395 A | 4/1999 | Yeung |
| 5,897,564 A | 4/1999 | Schulze et al. |
| 5,897,574 A | 4/1999 | Bonutti |
| 5,899,902 A | 5/1999 | Brown et al. |
| 5,899,938 A | 5/1999 | Sklar et al. |
| 5,908,421 A | 6/1999 | Beger |
| 5,908,436 A | 6/1999 | Cuschieri et al. |
| 5,910,148 A | 6/1999 | Reimels et al. |
| 5,911,721 A | 6/1999 | Nicholson et al. |
| 5,918,604 A | 7/1999 | Whelan |
| 5,921,986 A | 7/1999 | Bonutti |
| 5,925,008 A | 7/1999 | Douglas |
| 5,928,267 A | 7/1999 | Bonutti et al. |
| 5,931,838 A | 8/1999 | Vito |
| 5,931,844 A | 8/1999 | Thompson et al. |
| 5,931,869 A | 8/1999 | Boucher et al. |
| 5,935,149 A | 8/1999 | Ek |
| 5,938,668 A | 8/1999 | Scirica et al. |
| 5,941,439 A | 8/1999 | Kammerer et al. |
| 5,941,900 A | 8/1999 | Bonutti |
| 5,944,739 A | 8/1999 | Zlock et al. |
| 5,946,783 A | 9/1999 | Plociennik et al. |
| 5,947,915 A | 9/1999 | Thibodo, Jr. |
| 5,947,982 A | 9/1999 | Duran |
| 5,948,002 A | 9/1999 | Bonutti |
| 5,951,559 A | 9/1999 | Burkhart |
| 5,951,560 A | 9/1999 | Simon et al. |
| 5,954,747 A | 9/1999 | Clark |
| 5,957,953 A | 9/1999 | Dipoto et al. |
| 5,961,521 A | 10/1999 | Roger |
| 5,961,524 A | 10/1999 | Crombie |
| 5,964,764 A | 10/1999 | West, Jr. et al. |
| 5,964,767 A | 10/1999 | Tapia et al. |
| 5,964,783 A | 10/1999 | Grafton et al. |
| 5,968,045 A | 10/1999 | Frazier |
| 5,968,047 A | 10/1999 | Reed |
| 5,976,125 A | 11/1999 | Graham |
| 5,976,127 A | 11/1999 | Lax |
| 5,980,524 A | 11/1999 | Justin et al. |
| 5,980,539 A | 11/1999 | Kontos |
| 5,980,558 A | 11/1999 | Wiley |
| 5,980,559 A | 11/1999 | Bonutti |
| 5,989,252 A | 11/1999 | Fumex |
| 5,989,256 A | 11/1999 | Kuslich et al. |
| 5,989,282 A | 11/1999 | Bonutti |
| 5,993,452 A | 11/1999 | Vandewalle |
| 5,997,542 A | 12/1999 | Burke |
| 5,997,552 A | 12/1999 | Person et al. |
| 6,001,100 A | 12/1999 | Sherman et al. |
| 6,007,567 A | 12/1999 | Bonutti |
| 6,010,525 A | 1/2000 | Bonutti et al. |
| 6,016,727 A | 1/2000 | Morgan |
| 6,022,352 A | 2/2000 | Vandewalle |
| 6,022,373 A | 2/2000 | Li |
| 6,024,758 A | 2/2000 | Thal |
| 6,027,523 A | 2/2000 | Schmieding |
| 6,033,430 A | 3/2000 | Bonutti |
| 6,039,753 A | 3/2000 | Meislin |
| 6,041,485 A | 3/2000 | Pedlick et al. |
| 6,042,601 A | 3/2000 | Smith |
| 6,045,551 A | 4/2000 | Bonutti |
| 6,045,571 A | 4/2000 | Hill et al. |
| 6,045,573 A | 4/2000 | Wenstrom, Jr. et al. |
| 6,045,574 A | 4/2000 | Thal |
| 6,047,826 A | 4/2000 | Kalinski et al. |
| 6,048,343 A | 4/2000 | Mathis et al. |
| 6,051,006 A | 4/2000 | Shluzas et al. |
| 6,053,916 A | 4/2000 | Moore |
| 6,056,752 A | 5/2000 | Roger |
| 6,056,772 A | 5/2000 | Bonutti |
| 6,056,773 A | 5/2000 | Bonutti |
| 6,059,817 A | 5/2000 | Bonutti et al. |
| 6,062,344 A | 5/2000 | Okabe et al. |
| 6,068,648 A | 5/2000 | Cole et al. |
| 6,074,403 A | 6/2000 | Nord |
| 6,077,277 A | 6/2000 | Mollenauer et al. |
| 6,077,292 A | 6/2000 | Bonutti |
| 6,086,591 A | 7/2000 | Bojarski |
| 6,086,592 A | 7/2000 | Rosenberg et al. |
| 6,086,608 A | 7/2000 | Ek et al. |
| 6,096,060 A | 8/2000 | Fitts et al. |
| 6,099,530 A | 8/2000 | Simonian et al. |
| 6,099,568 A | 8/2000 | Simonian et al. |
| 6,106,545 A | 8/2000 | Egan et al. |
| 6,110,128 A | 8/2000 | Andelin et al. |
| 6,117,160 A | 9/2000 | Bonutti |
| 6,117,162 A | 9/2000 | Schmieding et al. |
| 6,123,710 A | 9/2000 | Pinczewski et al. |
| 6,132,433 A | 10/2000 | Whelan |
| 6,132,437 A | 10/2000 | Omurtag |
| 6,139,565 A | 10/2000 | Stone et al. |
| RE36,974 E | 11/2000 | Bonutti |
| 6,143,017 A | 11/2000 | Thal |
| 6,146,406 A | 11/2000 | Shluzas et al. |
| 6,146,408 A | 11/2000 | Bartlett |
| 6,149,653 A | 11/2000 | Deslauriers |
| 6,149,669 A | 11/2000 | Li |
| 6,152,928 A | 11/2000 | Wenstrom, Jr. |
| 6,152,934 A | 11/2000 | Harper et al. |
| 6,152,936 A | 11/2000 | Christy et al. |
| 6,152,949 A | 11/2000 | Bonutti |
| 6,156,039 A | 12/2000 | Thal |
| 6,156,056 A | 12/2000 | Kearns et al. |
| 6,159,234 A | 12/2000 | Bonutti et al. |
| 6,165,203 A | 12/2000 | Krebs |
| 6,168,598 B1 | 1/2001 | Martello |
| 6,168,628 B1 | 1/2001 | Huebner |
| 6,179,840 B1 | 1/2001 | Bowman |
| 6,183,461 B1 | 2/2001 | Matsuura et al. |
| 6,187,025 B1 | 2/2001 | Machek |
| 6,190,401 B1 | 2/2001 | Green et al. |
| 6,190,411 B1 | 2/2001 | Lo |
| 6,193,754 B1 | 2/2001 | Seedhom |
| 6,200,329 B1 | 3/2001 | Fung et al. |
| 6,200,330 B1 | 3/2001 | Benderev et al. |
| 6,203,565 B1 | 3/2001 | Bonutti et al. |
| 6,203,572 B1 | 3/2001 | Johnson et al. |
| 6,206,883 B1 | 3/2001 | Tunc |
| 6,210,376 B1 | 4/2001 | Grayson |
| 6,214,012 B1 | 4/2001 | Karpman et al. |
| 6,221,107 B1 | 4/2001 | Steiner |
| 6,228,096 B1 | 5/2001 | Marchand |
| 6,231,592 B1 | 5/2001 | Bonutti et al. |
| 6,235,057 B1 | 5/2001 | Roger et al. |
| 6,238,395 B1 | 5/2001 | Bonutti |
| 6,241,734 B1 | 6/2001 | Scribner et al. |
| 6,241,747 B1 | 6/2001 | Ruff |
| 6,241,771 B1 | 6/2001 | Gresser et al. |
| 6,245,081 B1 | 6/2001 | Bowman |
| 6,258,091 B1 | 7/2001 | Sevrain et al. |
| 6,267,766 B1 | 7/2001 | Burkhart |
| 6,269,716 B1 | 8/2001 | Amis |
| 6,270,518 B1 | 8/2001 | Pedlick et al. |
| 6,273,890 B1 | 8/2001 | Frazier |
| 6,283,973 B1 | 9/2001 | Hubbard et al. |
| 6,283,996 B1 | 9/2001 | Chervitz et al. |
| 6,287,325 B1 | 9/2001 | Bonutti |
| 6,293,961 B2 | 9/2001 | Schwartz et al. |
| 6,296,659 B1 | 10/2001 | Foerster |
| 6,299,615 B1 | 10/2001 | Huebner |
| 6,302,888 B1 | 10/2001 | Mellinger et al. |
| 6,306,156 B1 | 10/2001 | Clark |
| 6,306,159 B1 | 10/2001 | Schwartz et al. |
| 6,309,405 B1 | 10/2001 | Bonutti |
| 6,312,448 B1 | 11/2001 | Bonutti |
| 6,319,271 B1 | 11/2001 | Schwartz et al. |

(56) References Cited

U.S. PATENT DOCUMENTS

| | | |
|---|---|---|
| 6,328,758 B1 | 12/2001 | Tornier et al. |
| 6,342,060 B1 | 1/2002 | Adams |
| 6,343,531 B2 | 2/2002 | Amis |
| 6,364,897 B1 | 4/2002 | Bonutti |
| 6,368,322 B1 | 4/2002 | Luks et al. |
| 6,368,326 B1 | 4/2002 | Dakin et al. |
| 6,368,343 B1 | 4/2002 | Bonutti et al. |
| 6,371,124 B1 | 4/2002 | Whelan |
| 6,379,361 B1 | 4/2002 | Beck, Jr. et al. |
| 6,383,190 B1 | 5/2002 | Preissman |
| 6,383,199 B2 | 5/2002 | Carter et al. |
| 6,387,113 B1 | 5/2002 | Hawkins et al. |
| 6,387,129 B2 | 5/2002 | Rieser et al. |
| 6,398,785 B2 | 6/2002 | Carchidi et al. |
| 6,406,479 B1 | 6/2002 | Justin et al. |
| 6,409,743 B1 | 6/2002 | Fenton, Jr. |
| 6,413,260 B1 | 7/2002 | Berrevoets et al. |
| 6,423,088 B1 | 7/2002 | Fenton, Jr. |
| 6,428,562 B2 | 8/2002 | Bonutti |
| 6,432,123 B2 | 8/2002 | Schwartz et al. |
| 6,436,124 B1 | 8/2002 | Anderson et al. |
| 6,440,134 B1 | 8/2002 | Zaccherotti et al. |
| 6,440,136 B1 | 8/2002 | Gambale et al. |
| 6,447,516 B1 | 9/2002 | Bonutti |
| 6,451,030 B2 | 9/2002 | Li et al. |
| 6,454,768 B1 | 9/2002 | Jackson |
| 6,458,134 B1 | 10/2002 | Songer et al. |
| 6,461,373 B2 | 10/2002 | Wyman et al. |
| 6,464,713 B2 | 10/2002 | Bonutti |
| 6,468,293 B2 | 10/2002 | Bonutti et al. |
| 6,471,707 B1 | 10/2002 | Miller et al. |
| 6,475,230 B1 | 11/2002 | Bonutti et al. |
| 6,482,210 B1 | 11/2002 | Skiba et al. |
| 6,485,504 B1 | 11/2002 | Johnson et al. |
| 6,497,901 B1 | 12/2002 | Royer |
| 6,500,184 B1 | 12/2002 | Chan et al. |
| 6,500,195 B2 | 12/2002 | Bonutti |
| RE37,963 E | 1/2003 | Thal |
| 6,503,267 B2 | 1/2003 | Bonutti et al. |
| 6,508,820 B2 | 1/2003 | Bales |
| 6,508,821 B1 | 1/2003 | Schwartz et al. |
| 6,508,830 B2 | 1/2003 | Steiner |
| 6,511,498 B1 | 1/2003 | Fumex |
| 6,511,499 B2 | 1/2003 | Schmieding et al. |
| 6,517,542 B1 | 2/2003 | Papay et al. |
| 6,517,552 B1 | 2/2003 | Nord et al. |
| 6,517,578 B2 | 2/2003 | Hein |
| 6,517,579 B1 | 2/2003 | Paulos et al. |
| 6,520,964 B2 | 2/2003 | Tallarida et al. |
| 6,520,980 B1 | 2/2003 | Foerster |
| 6,524,317 B1 | 2/2003 | Ritchart et al. |
| 6,527,777 B2 | 3/2003 | Justin |
| 6,527,794 B1 | 3/2003 | Mcdevitt et al. |
| 6,527,795 B1 | 3/2003 | Lizardi |
| 6,533,795 B1 | 3/2003 | Tran et al. |
| 6,533,802 B2 | 3/2003 | Bojarski et al. |
| 6,537,319 B2 | 3/2003 | Whelan |
| 6,540,750 B2 | 4/2003 | Burkhart |
| 6,540,770 B1 | 4/2003 | Tornier et al. |
| 6,544,281 B2 | 4/2003 | Elattrache et al. |
| 6,547,564 B1 | 4/2003 | Hansson |
| 6,547,800 B2 | 4/2003 | Foerster et al. |
| 6,551,330 B1 | 4/2003 | Bain et al. |
| 6,551,343 B1 | 4/2003 | Tormala et al. |
| 6,553,802 B1 | 4/2003 | Jacob |
| 6,554,830 B1 | 4/2003 | Chappius |
| 6,554,852 B1 | 4/2003 | Oberlander |
| 6,554,862 B2 | 4/2003 | Hays et al. |
| 6,562,071 B2 | 5/2003 | Järvinen |
| 6,565,572 B2 | 5/2003 | Chappius |
| 6,565,573 B1 | 5/2003 | Ferrante |
| 6,569,186 B1 | 5/2003 | Winters et al. |
| 6,569,187 B1 | 5/2003 | Bonutti et al. |
| 6,572,635 B1 | 6/2003 | Bonutti |
| 6,575,925 B1 | 6/2003 | Noble |
| 6,579,295 B1 | 6/2003 | Supinski |
| 6,582,453 B1 | 6/2003 | Tran et al. |
| 6,585,730 B1 | 7/2003 | Foerster |
| 6,585,740 B2 | 7/2003 | Schlapfer et al. |
| 6,585,750 B2 | 7/2003 | Bonutti et al. |
| 6,589,245 B1 | 7/2003 | Weiler et al. |
| 6,589,246 B1 | 7/2003 | Hack et al. |
| 6,592,609 B1 | 7/2003 | Bonutti |
| 6,595,911 B2 | 7/2003 | Lovuolo |
| 6,599,289 B1 | 7/2003 | Bojarski et al. |
| 6,605,096 B1 | 8/2003 | Ritchart |
| 6,607,548 B2 | 8/2003 | Pohjonen et al. |
| 6,610,079 B1 | 8/2003 | Li et al. |
| 6,613,018 B2 | 9/2003 | Bagga et al. |
| 6,616,694 B1 | 9/2003 | Hart |
| 6,620,166 B1 | 9/2003 | Wenstrom, Jr. et al. |
| 6,620,185 B1 | 9/2003 | Harvie et al. |
| 6,620,195 B2 | 9/2003 | Goble et al. |
| 6,620,329 B2 | 9/2003 | Rosen et al. |
| 6,620,349 B1 | 9/2003 | Lopez |
| 6,623,492 B1 | 9/2003 | Berube et al. |
| 6,623,524 B2 | 9/2003 | Schmieding |
| 6,626,910 B1 | 9/2003 | Hugues |
| 6,626,919 B1 | 9/2003 | Swanstrom |
| 6,629,977 B1 | 10/2003 | Wolf |
| 6,635,073 B2 | 10/2003 | Bonutti |
| 6,638,279 B2 | 10/2003 | Bonutti |
| 6,641,596 B1 | 11/2003 | Lizardi |
| 6,641,597 B2 | 11/2003 | Burkhart et al. |
| 6,645,227 B2 | 11/2003 | Fallin et al. |
| 6,652,562 B2 | 11/2003 | Collier et al. |
| 6,652,563 B2 | 11/2003 | Dreyfuss |
| 6,656,182 B1 | 12/2003 | Hayhurst |
| 6,656,183 B2 | 12/2003 | Colleran et al. |
| 6,658,182 B1 | 12/2003 | Gonthier |
| 6,660,008 B1 | 12/2003 | Foerster et al. |
| 6,660,022 B1 | 12/2003 | Li et al. |
| 6,663,634 B2 | 12/2003 | Ahrens et al. |
| 6,663,656 B2 | 12/2003 | Schmieding et al. |
| 6,666,868 B2 | 12/2003 | Fallin |
| 6,682,549 B2 | 1/2004 | Bartlett |
| 6,685,728 B2 | 2/2004 | Sinnott et al. |
| 6,689,137 B2 | 2/2004 | Reed |
| 6,689,154 B2 | 2/2004 | Bartlett |
| 6,692,499 B2 | 2/2004 | Tormala et al. |
| 6,712,849 B2 | 3/2004 | Re et al. |
| 6,716,224 B2 | 4/2004 | Singhatat |
| 6,716,957 B2 | 4/2004 | Tunc |
| 6,730,092 B2 | 5/2004 | Songer |
| 6,730,124 B2 | 5/2004 | Steiner |
| 6,736,799 B1 | 5/2004 | Erbe et al. |
| 6,746,483 B1 | 6/2004 | Bojarski et al. |
| 6,755,836 B1 | 6/2004 | Lewis |
| 6,761,739 B2 | 7/2004 | Shepard |
| 6,767,037 B2 | 7/2004 | Wenstrom, Jr. |
| 6,770,076 B2 | 8/2004 | Foerster |
| 6,770,084 B1 | 8/2004 | Bain et al. |
| 6,773,450 B2 | 8/2004 | Leung et al. |
| 6,780,190 B2 | 8/2004 | Maroney |
| 6,780,198 B1 | 8/2004 | Gregoire et al. |
| 6,802,862 B1 | 10/2004 | Roger et al. |
| 6,808,502 B2 | 10/2004 | Nguyen |
| 6,808,526 B1 | 10/2004 | Magerl et al. |
| 6,814,741 B2 | 11/2004 | Bowman et al. |
| 6,830,572 B2 | 12/2004 | Mcdevitt et al. |
| 6,833,005 B1 | 12/2004 | Mantas |
| 6,840,953 B2 | 1/2005 | Martinek |
| 6,860,885 B2 | 3/2005 | Bonutti |
| 6,863,671 B1 | 3/2005 | Strobel et al. |
| 6,872,040 B2 | 3/2005 | Deeg et al. |
| 6,875,216 B2 | 4/2005 | Wolf |
| 6,884,249 B2 | 4/2005 | May et al. |
| 6,887,259 B2 | 5/2005 | Lizardi |
| 6,890,354 B2 | 5/2005 | Steiner et al. |
| 6,893,448 B2 | 5/2005 | O'quinn et al. |
| 6,896,686 B2 | 5/2005 | Weber |
| 6,899,722 B2 | 5/2005 | Bonutti |
| 6,902,573 B2 | 6/2005 | Strobel et al. |
| 6,908,466 B1 | 6/2005 | Bonutti et al. |

(56) References Cited

U.S. PATENT DOCUMENTS

| | | |
|---|---|---|
| 6,916,292 B2 | 7/2005 | Morawski et al. |
| 6,916,321 B2 | 7/2005 | Tenhuisen et al. |
| 6,921,402 B2 | 7/2005 | Contiliano et al. |
| 6,923,823 B1 | 8/2005 | Bartlett et al. |
| 6,923,824 B2 | 8/2005 | Morgan et al. |
| 6,951,565 B2 | 10/2005 | Keane et al. |
| 6,972,027 B2 | 12/2005 | Fallin et al. |
| 6,980,903 B2 | 12/2005 | Daniels et al. |
| 6,986,781 B2 | 1/2006 | Smith |
| 6,989,034 B2 | 1/2006 | Hammer et al. |
| 7,066,942 B2 | 6/2006 | Treace |
| 7,066,944 B2 | 6/2006 | Laufer et al. |
| 7,105,010 B2 | 9/2006 | Hart et al. |
| 7,112,221 B2 | 9/2006 | Harris |
| 7,118,583 B2 | 10/2006 | O'quinn et al. |
| 7,137,996 B2 | 11/2006 | Steiner et al. |
| 7,141,066 B2 | 11/2006 | Steiner et al. |
| 7,153,307 B2 | 12/2006 | Scribner |
| 7,153,312 B1 | 12/2006 | Torrie et al. |
| 7,201,722 B2 | 4/2007 | Krueger |
| 7,235,091 B2 | 6/2007 | Thornes |
| 7,255,675 B2 | 8/2007 | Gertner et al. |
| 7,261,716 B2 | 8/2007 | Strobel et al. |
| 7,264,634 B2 | 9/2007 | Schmieding |
| 7,285,124 B2 | 10/2007 | Foerster |
| 7,306,417 B2 | 12/2007 | Dorstewitz |
| 7,326,222 B2 | 2/2008 | Dreyfuss et al. |
| 7,390,332 B2 | 6/2008 | Selvitelli et al. |
| 7,481,825 B2 | 1/2009 | Bonutti |
| 7,500,983 B1 | 3/2009 | Kaiser et al. |
| 7,601,165 B2 | 10/2009 | Stone |
| 7,608,098 B1 | 10/2009 | Stone et al. |
| 7,615,076 B2 | 11/2009 | Cauthen, III et al. |
| 7,632,287 B2 | 12/2009 | Baker et al. |
| 7,651,509 B2 | 1/2010 | Bojarski et al. |
| 7,658,751 B2 | 2/2010 | Stone et al. |
| 7,670,279 B2 | 3/2010 | Gertner |
| 7,678,123 B2 | 3/2010 | Chanduszko |
| 7,695,493 B2 | 4/2010 | Saadat et al. |
| 7,736,379 B2 | 6/2010 | Ewers et al. |
| 7,749,259 B2 | 7/2010 | Lim et al. |
| 7,758,594 B2 | 7/2010 | Lamson et al. |
| 7,776,041 B1 | 8/2010 | Walters |
| 7,819,895 B2 | 10/2010 | Ginn et al. |
| 7,875,058 B2 | 1/2011 | Holmes, Jr. |
| 8,317,825 B2 | 11/2012 | Stone |
| 8,439,918 B2 | 5/2013 | Gelfand |
| 8,574,268 B2 | 11/2013 | Chan et al. |
| 8,672,969 B2 | 3/2014 | Stone et al. |
| 9,259,217 B2 | 2/2016 | Fritzinger |
| 2001/0014825 A1 | 8/2001 | Burke et al. |
| 2001/0037131 A1 | 11/2001 | Schmieding et al. |
| 2001/0037153 A1 | 11/2001 | Rockwood et al. |
| 2001/0041916 A1 | 11/2001 | Bonutti |
| 2001/0041937 A1 | 11/2001 | Rieser et al. |
| 2001/0041938 A1 | 11/2001 | Hein |
| 2001/0044639 A1 | 11/2001 | Levinson |
| 2001/0047206 A1 | 11/2001 | Sklar et al. |
| 2001/0051816 A1 | 12/2001 | Enzerink et al. |
| 2001/0053934 A1 | 12/2001 | Schmieding |
| 2002/0001964 A1 | 1/2002 | Choi |
| 2002/0004669 A1 | 1/2002 | Bartlett |
| 2002/0007182 A1 | 1/2002 | Kim |
| 2002/0010513 A1 | 1/2002 | Schmieding |
| 2002/0013608 A1 | 1/2002 | Elattrache et al. |
| 2002/0019649 A1 | 2/2002 | Sikora et al. |
| 2002/0055780 A1 | 5/2002 | Sklar |
| 2002/0058966 A1 | 5/2002 | Tormala et al. |
| 2002/0099411 A1 | 7/2002 | Bartlett |
| 2002/0111653 A1 | 8/2002 | Foerster |
| 2002/0120270 A1 | 8/2002 | Trieu et al. |
| 2002/0120292 A1 | 8/2002 | Morgan |
| 2002/0123752 A1 | 9/2002 | Schultheiss et al. |
| 2002/0128684 A1 | 9/2002 | Foerster |
| 2002/0147463 A1 | 10/2002 | Martinek |
| 2002/0161401 A1 | 10/2002 | Steiner |
| 2002/0161439 A1 | 10/2002 | Strobel et al. |
| 2002/0169452 A1 | 11/2002 | Tormala et al. |
| 2002/0169477 A1 | 11/2002 | Demopulos et al. |
| 2002/0169478 A1 | 11/2002 | Schwartz et al. |
| 2002/0173788 A1 | 11/2002 | Bojarski et al. |
| 2002/0188298 A1 | 12/2002 | Chan |
| 2003/0023268 A1 | 1/2003 | Lizardi |
| 2003/0032961 A1 | 2/2003 | Pelo et al. |
| 2003/0033021 A1 | 2/2003 | Plouhar et al. |
| 2003/0033022 A1 | 2/2003 | Plouhar et al. |
| 2003/0036797 A1 | 2/2003 | Malaviya et al. |
| 2003/0036801 A1 | 2/2003 | Schwartz et al. |
| 2003/0065391 A1 | 4/2003 | Re et al. |
| 2003/0078603 A1 | 4/2003 | Schaller et al. |
| 2003/0078617 A1 | 4/2003 | Schwartz et al. |
| 2003/0083662 A1 | 5/2003 | Middleton |
| 2003/0088251 A1 | 5/2003 | Braun et al. |
| 2003/0088272 A1 | 5/2003 | Smith |
| 2003/0105477 A1 | 6/2003 | Schwartz et al. |
| 2003/0120309 A1 | 6/2003 | Colleran et al. |
| 2003/0130694 A1 | 7/2003 | Bojarski et al. |
| 2003/0135214 A1 | 7/2003 | Fetto et al. |
| 2003/0135239 A1 | 7/2003 | Gabriel et al. |
| 2003/0135963 A1 | 7/2003 | Holbrook et al. |
| 2003/0152522 A1 | 8/2003 | Miller et al. |
| 2003/0167072 A1 | 9/2003 | Oberlander |
| 2003/0167090 A1 | 9/2003 | Chervitz et al. |
| 2003/0171811 A1 | 9/2003 | Steiner et al. |
| 2003/0176865 A1 | 9/2003 | Supinski |
| 2003/0176919 A1 | 9/2003 | Schmieding |
| 2003/0181925 A1 | 9/2003 | Bain et al. |
| 2003/0195528 A1 | 10/2003 | Ritchart |
| 2003/0208210 A1 | 11/2003 | Dreyfuss et al. |
| 2003/0220660 A1 | 11/2003 | Kortenbach et al. |
| 2003/0225459 A1 | 12/2003 | Hammer et al. |
| 2004/0002734 A1 | 1/2004 | Fallin et al. |
| 2004/0006345 A1 | 1/2004 | Vlahos et al. |
| 2004/0006346 A1 | 1/2004 | Holmen et al. |
| 2004/0015171 A1 | 1/2004 | Bojarski et al. |
| 2004/0015172 A1 | 1/2004 | Biedermann et al. |
| 2004/0024456 A1 | 2/2004 | Charles, Jr. et al. |
| 2004/0087981 A1 | 5/2004 | Berube et al. |
| 2004/0092936 A1 | 5/2004 | Miller et al. |
| 2004/0098051 A1 | 5/2004 | Fallin et al. |
| 2004/0111117 A1 | 6/2004 | Colleran et al. |
| 2004/0122431 A1 | 6/2004 | Biedermann et al. |
| 2004/0127907 A1 | 7/2004 | Dakin et al. |
| 2004/0133211 A1 | 7/2004 | Raskin et al. |
| 2004/0138664 A1 | 7/2004 | Bowman |
| 2004/0138683 A1 | 7/2004 | Shelton et al. |
| 2004/0138704 A1 | 7/2004 | Gambale et al. |
| 2004/0138706 A1 | 7/2004 | Abrams et al. |
| 2004/0143344 A1 | 7/2004 | Malaviya et al. |
| 2004/0153103 A1 | 8/2004 | Schwartz et al. |
| 2004/0153153 A1 | 8/2004 | Elson et al. |
| 2004/0162579 A1 | 8/2004 | Foerster |
| 2004/0166169 A1 | 8/2004 | Malaviya et al. |
| 2004/0182968 A1 | 9/2004 | Gentry |
| 2004/0220574 A1 | 11/2004 | Pelo et al. |
| 2004/0225292 A1 | 11/2004 | Sasso et al. |
| 2004/0236353 A1 | 11/2004 | Bain et al. |
| 2004/0243139 A1 | 12/2004 | Lewis et al. |
| 2004/0243178 A1 | 12/2004 | Haut et al. |
| 2004/0249394 A1 | 12/2004 | Morris et al. |
| 2004/0267164 A1 | 12/2004 | Rhodes et al. |
| 2004/0267265 A1 | 12/2004 | Kyle |
| 2004/0267270 A1 | 12/2004 | Jacobs et al. |
| 2004/0267276 A1 | 12/2004 | Camino et al. |
| 2004/0267277 A1 | 12/2004 | Zannis et al. |
| 2004/0267304 A1 | 12/2004 | Zannis et al. |
| 2005/0027307 A1 | 2/2005 | Schwartz et al. |
| 2005/0033363 A1 | 2/2005 | Bojarski et al. |
| 2005/0038426 A1 | 2/2005 | Chan |
| 2005/0055027 A1 | 3/2005 | Yeung et al. |
| 2005/0064042 A1 | 3/2005 | Vunjak-novakovic et al. |
| 2005/0074495 A1 | 4/2005 | Schwartz et al. |
| 2005/0090828 A1 | 4/2005 | Alford |
| 2005/0096696 A1 | 5/2005 | Forsberg |

(56) References Cited

U.S. PATENT DOCUMENTS

| | | |
|---|---|---|
| 2005/0096697 A1 | 5/2005 | Forsberg et al. |
| 2005/0107828 A1 | 5/2005 | Reese |
| 2005/0119531 A1 | 6/2005 | Sharratt |
| 2005/0125073 A1 | 6/2005 | Orban et al. |
| 2005/0137600 A1 | 6/2005 | Jacobs et al. |
| 2005/0149033 A1 | 7/2005 | Mcguire et al. |
| 2005/0159812 A1 | 7/2005 | Dinger, III et al. |
| 2005/0165416 A1 | 7/2005 | Bojarski et al. |
| 2005/0165482 A1 | 7/2005 | Goldhahn et al. |
| 2005/0187565 A1 | 8/2005 | Baker et al. |
| 2005/0203620 A1 | 9/2005 | Steiner et al. |
| 2005/0222618 A1 | 10/2005 | Dreyfuss et al. |
| 2005/0222619 A1 | 10/2005 | Dreyfuss et al. |
| 2005/0228448 A1 | 10/2005 | Li |
| 2005/0267479 A1 | 12/2005 | Morgan et al. |
| 2005/0267533 A1 | 12/2005 | Gertner |
| 2005/0277961 A1 | 12/2005 | Stone et al. |
| 2005/0283040 A1 | 12/2005 | Greenhalgh |
| 2005/0283156 A1 | 12/2005 | Schmieding et al. |
| 2005/0283158 A1 | 12/2005 | West, Jr. |
| 2005/0283192 A1 | 12/2005 | Torrie et al. |
| 2006/0030884 A1 | 2/2006 | Yeung et al. |
| 2006/0030948 A1 | 2/2006 | Manrique et al. |
| 2006/0036265 A1 | 2/2006 | Dant et al. |
| 2006/0064126 A1 | 3/2006 | Fallin et al. |
| 2006/0069334 A1 | 3/2006 | Moskowitz |
| 2006/0084943 A1 | 4/2006 | Rosenman et al. |
| 2006/0100627 A1 | 5/2006 | Stone et al. |
| 2006/0121084 A1 | 6/2006 | Borden et al. |
| 2006/0135958 A1 | 6/2006 | Marissen et al. |
| 2006/0167481 A1 | 7/2006 | Baker et al. |
| 2006/0167482 A1 | 7/2006 | Swain et al. |
| 2006/0178680 A1 | 8/2006 | Nelson et al. |
| 2006/0189993 A1 | 8/2006 | Stone |
| 2006/0190041 A1 | 8/2006 | Fallin et al. |
| 2006/0190042 A1 | 8/2006 | Stone et al. |
| 2006/0229671 A1 | 10/2006 | Steiner et al. |
| 2006/0247642 A1 | 11/2006 | Stone et al. |
| 2006/0253130 A1 | 11/2006 | Wolniewicz, III |
| 2006/0271192 A1 | 11/2006 | Olsen et al. |
| 2006/0276896 A1 | 12/2006 | Fallin et al. |
| 2006/0280768 A1 | 12/2006 | Hwang et al. |
| 2006/0282085 A1 | 12/2006 | Stone |
| 2006/0293709 A1 | 12/2006 | Bojarski et al. |
| 2007/0005080 A1 | 1/2007 | Wolniewicz, III et al. |
| 2007/0016305 A1 | 1/2007 | Chudik |
| 2007/0055255 A1 | 3/2007 | Siegel |
| 2007/0060922 A1 | 3/2007 | Dreyfuss |
| 2007/0067025 A1 | 3/2007 | Schwartz |
| 2007/0073307 A1 | 3/2007 | Scribner et al. |
| 2007/0073342 A1 | 3/2007 | Stone et al. |
| 2007/0078435 A1 | 4/2007 | Stone et al. |
| 2007/0083236 A1 | 4/2007 | Sikora et al. |
| 2007/0093847 A1 | 4/2007 | Scribner et al. |
| 2007/0142838 A1 | 6/2007 | Jordan |
| 2007/0179531 A1 | 8/2007 | Thornes |
| 2007/0185532 A1 | 8/2007 | Stone et al. |
| 2007/0239209 A1 | 10/2007 | Fallman |
| 2007/0239275 A1 | 10/2007 | Willobee |
| 2007/0250163 A1 | 10/2007 | Cassani |
| 2007/0270853 A1 | 11/2007 | Leung |
| 2008/0027446 A1 | 1/2008 | Stone et al. |
| 2008/0046009 A1 | 2/2008 | Albertorio et al. |
| 2008/0065114 A1 | 3/2008 | Stone et al. |
| 2008/0082127 A1 | 4/2008 | Stone et al. |
| 2008/0082128 A1 | 4/2008 | Stone |
| 2008/0132753 A1 | 6/2008 | Goddard |
| 2008/0132932 A1 | 6/2008 | Hoeppner et al. |
| 2008/0140092 A1 | 6/2008 | Stone et al. |
| 2008/0140093 A1 | 6/2008 | Stone et al. |
| 2008/0161852 A1 | 7/2008 | Kaiser et al. |
| 2008/0177302 A1 | 7/2008 | Shurnas |
| 2008/0188936 A1 | 8/2008 | Ball et al. |
| 2008/0208252 A1 | 8/2008 | Holmes |
| 2008/0255613 A1 | 10/2008 | Kaiser et al. |
| 2008/0268064 A1 | 10/2008 | Woodell-may |
| 2008/0269674 A1 | 10/2008 | Stone |
| 2008/0275477 A1 | 11/2008 | Sterrett et al. |
| 2008/0312689 A1 | 12/2008 | Denham et al. |
| 2009/0054928 A1 | 2/2009 | Denham et al. |
| 2009/0062854 A1 | 3/2009 | Kaiser et al. |
| 2009/0082805 A1 | 3/2009 | Kaiser et al. |
| 2009/0177233 A1 | 7/2009 | Malek |
| 2009/0192468 A1 | 7/2009 | Stone |
| 2009/0204146 A1 | 8/2009 | Kaiser et al. |
| 2009/0287215 A1 | 11/2009 | Fisher et al. |
| 2009/0306711 A1 | 12/2009 | Stone et al. |
| 2009/0312776 A1 | 12/2009 | Kaiser et al. |
| 2009/0318961 A1 | 12/2009 | Stone et al. |
| 2010/0016899 A1* | 1/2010 | Gelfand ............ A61B 17/0401 606/280 |
| 2010/0042114 A1 | 2/2010 | Schaffhausen et al. |
| 2010/0087857 A1 | 4/2010 | Stone et al. |
| 2010/0145384 A1 | 6/2010 | Stone et al. |
| 2010/0211075 A1 | 8/2010 | Stone |
| 2010/0256677 A1 | 10/2010 | Albertorio et al. |
| 2010/0262185 A1* | 10/2010 | Gelfand ............ A61B 17/0401 606/232 |
| 2010/0268275 A1 | 10/2010 | Stone et al. |
| 2010/0292792 A1 | 11/2010 | Stone et al. |
| 2010/0305698 A1 | 12/2010 | Metzger et al. |
| 2010/0305709 A1 | 12/2010 | Metzger et al. |
| 2010/0312341 A1 | 12/2010 | Kaiser et al. |
| 2011/0071573 A1 | 3/2011 | Sixto et al. |
| 2011/0087284 A1 | 4/2011 | Stone et al. |
| 2011/0098727 A1 | 4/2011 | Kaiser et al. |
| 2012/0150235 A1* | 6/2012 | Snyder ............... A61B 17/0401 606/289 |
| 2012/0226322 A1* | 9/2012 | Gonzalez-Hernandez ......... A61B 17/8061 606/286 |
| 2013/0123841 A1* | 5/2013 | Lyon ................. A61B 17/0401 606/232 |
| 2013/0172944 A1* | 7/2013 | Fritzinger ......... A61B 17/0401 606/286 |

FOREIGN PATENT DOCUMENTS

| | | |
|---|---|---|
| AU | 5850469 A | 1/1971 |
| AU | 5963869 A | 2/1971 |
| AU | 1505470 A | 11/1971 |
| AU | 2223767 A | 5/1973 |
| AU | 3615171 A | 5/1973 |
| AU | 5028569 A | 9/1973 |
| AU | 7110887 A | 10/1987 |
| AU | 1713188 A | 11/1989 |
| AU | 3877493 B2 | 8/1994 |
| DE | 2529669 A1 | 3/1976 |
| DE | 2747312 A1 | 4/1979 |
| DE | 2818254 A1 | 10/1979 |
| DE | 2919009 A1 | 11/1979 |
| DE | 3027138 A1 | 12/1981 |
| DE | 3225620 A1 | 2/1983 |
| DE | 3136083 A1 | 3/1983 |
| DE | 233303 | 2/1986 |
| DE | 4127550 A1 | 2/1993 |
| DE | 4302397 A | 7/1993 |
| DE | 29621340 U1 | 4/1998 |
| DE | 19841252 A1 | 3/2000 |
| EP | 0108912 A2 | 5/1984 |
| EP | 0129422 A2 | 12/1984 |
| EP | 0129442 A1 | 12/1984 |
| EP | 0172130 A2 | 2/1986 |
| EP | 0241240 A2 | 10/1987 |
| EP | 0241792 A1 | 10/1987 |
| EP | 0260970 A2 | 3/1988 |
| EP | 0270704 A1 | 6/1988 |
| EP | 0282789 A2 | 9/1988 |
| EP | 0315371 A2 | 5/1989 |
| EP | 0317406 A1 | 5/1989 |
| EP | 0340159 A1 | 11/1989 |
| EP | 0346183 A1 | 12/1989 |
| EP | 0349173 A1 | 1/1990 |
| EP | 0374088 A1 | 6/1990 |

(56) References Cited

FOREIGN PATENT DOCUMENTS

| | | |
|---|---|---|
| EP | 0409364 A2 | 1/1991 |
| EP | 0415915 A1 | 3/1991 |
| EP | 0440991 A1 | 8/1991 |
| EP | 0441065 A2 | 8/1991 |
| EP | 0451932 A1 | 10/1991 |
| EP | 0464480 A1 | 1/1992 |
| EP | 0490417 A1 | 6/1992 |
| EP | 0497079 A1 | 8/1992 |
| EP | 0502509 A1 | 9/1992 |
| EP | 0502698 A1 | 9/1992 |
| EP | 520177 A1 | 12/1992 |
| EP | 0546726 A1 | 6/1993 |
| EP | 0574707 A1 | 12/1993 |
| EP | 0582514 A1 | 2/1994 |
| EP | 0591991 A2 | 4/1994 |
| EP | 0598219 A2 | 5/1994 |
| EP | 0611551 A1 | 8/1994 |
| EP | 0627203 A2 | 12/1994 |
| EP | 0651979 A1 | 5/1995 |
| EP | 0669110 A2 | 8/1995 |
| EP | 0686373 A1 | 12/1995 |
| EP | 0702933 A1 | 3/1996 |
| EP | 0775473 A1 | 5/1997 |
| EP | 0913123 A1 | 5/1999 |
| EP | 0913131 A2 | 5/1999 |
| EP | 0995409 A1 | 4/2000 |
| EP | 1013229 A2 | 6/2000 |
| EP | 1093773 A1 | 4/2001 |
| EP | 1093774 A1 | 4/2001 |
| EP | 1555945 A2 | 7/2005 |
| EP | 2455002 A1 | 5/2012 |
| FR | 2622790 A1 | 5/1989 |
| FR | 2655840 A1 | 6/1991 |
| FR | 2682867 A1 | 4/1993 |
| FR | 2687911 A1 | 9/1993 |
| FR | 2688689 A1 | 9/1993 |
| FR | 2704140 A3 | 10/1994 |
| FR | 2717070 A1 | 9/1995 |
| FR | 2723528 A1 | 2/1996 |
| FR | 2744010 A1 | 8/1997 |
| FR | 2745999 A1 | 9/1997 |
| FR | 2770764 A1 | 5/1999 |
| GB | 401677 A | 11/1933 |
| GB | 1413477 A | 11/1975 |
| GB | 1485681 A | 9/1977 |
| GB | 2083751 A | 3/1982 |
| GB | 2118474 A | 11/1983 |
| GB | 2227175 A | 7/1990 |
| GB | 2253147 A | 9/1992 |
| GB | 2312376 A | 10/1997 |
| GB | 2403416 A | 1/2005 |
| JP | 5362911 A | 7/1987 |
| JP | 62159647 A | 7/1987 |
| JP | 62295657 A | 12/1987 |
| JP | 5269160 A | 10/1993 |
| JP | 5300917 A | 11/1993 |
| JP | 751292 A | 2/1995 |
| JP | 10211213 A | 8/1998 |
| JP | 5362912 B2 | 12/2013 |
| JP | 5374942 B2 | 12/2013 |
| JP | 5378230 B2 | 12/2013 |
| WO | WO-8300615 A1 | 3/1983 |
| WO | WO-8603666 A1 | 7/1986 |
| WO | WO-8701270 A1 | 3/1987 |
| WO | WO-8901767 A1 | 3/1989 |
| WO | WO-8909030 A1 | 10/1989 |
| WO | WO-8910096 A1 | 11/1989 |
| WO | WO-9008510 A1 | 8/1990 |
| WO | WO-9203980 A1 | 3/1992 |
| WO | WO-9314705 A1 | 8/1993 |
| WO | WO-9315694 A1 | 8/1993 |
| WO | WO-9502373 A1 | 1/1995 |
| WO | WO-9503003 A1 | 2/1995 |
| WO | WO-9529637 A1 | 11/1995 |
| WO | WO-9532670 A1 | 12/1995 |
| WO | WO-9629029 A1 | 9/1996 |
| WO | WO-9737603 A1 | 10/1997 |
| WO | WO-9812991 A1 | 4/1998 |
| WO | WO-9812992 A1 | 4/1998 |
| WO | WO-9822047 A1 | 5/1998 |
| WO | WO-9822048 A1 | 5/1998 |
| WO | WO-9901084 A2 | 1/1999 |
| WO | WO-9912480 A1 | 3/1999 |
| WO | WO-9944544 A1 | 9/1999 |
| WO | WO-0040159 A1 | 7/2000 |
| WO | WO-0139671 A1 | 6/2001 |
| WO | WO-0236020 A1 | 5/2002 |
| WO | WO-03005914 A1 | 1/2003 |
| WO | WO-03071962 A2 | 9/2003 |
| WO | WO-03077772 A1 | 9/2003 |
| WO | WO-2005104992 A1 | 11/2005 |
| WO | WO-2011040917 A1 | 4/2011 |
| WO | WO-2013103474 A1 | 7/2013 |

OTHER PUBLICATIONS

U.S. Appl. No. 13/342,646, Non Final Office Action mailed Mar. 26, 2014, 10 pgs.
U.S. Appl. No. 13/342,646, Non Final Office Action mailed Sep. 17, 2014, 7 pgs.
U.S. Appl. No. 13/342,646, Notice of Allowance mailed Oct. 7, 2015, 5 pgs.
U.S. Appl. No. 13/342,646, Response filed Jun. 25, 2014 to Non Final Office Action mailed Mar. 26, 2014, 16 pgs.
U.S. Appl. No. 13/342,646, Response filed Jul. 24, 2015 to Non Final Office Action mailed Mar. 4, 2015, 18 pgs.
U.S. Appl. No. 13/342,646, Response filed Nov. 13, 2014 to Non Final Office Action mailed Sep. 17, 2014, 11 pgs.
"Arthrex Tightrope", Biomet Orthopedics, (2009), 1 pg.
"Bio-Intrafix Tibial Soft Tissue Fastener, Building on the Legacy of IntraFix", DePuy Mitek brochure, (Feb. 2007), 6 pgs.
"Biomet Toggleloc", Biomet Orthopedics, (2009), 1 pg.
"Do your next distal tendon repair with . . . The Lubbers Technique", Teno Fix@ brochure, Ortheon® Medical, (2003), 2 pgs.
European Application Serial No. 12813617.3, Office Action mailed Sep. 11, 2014, 2 pgs.
European Application Serial No. 12813617.3, Response filed Sep. 27, 2015 to Office Action mailed Sep. 11, 2014, 12 pgs.
"EZ Loc Femoral Fixation Device", copyright 2005 Arthrotek, Inc, (2005), 8 pgs.
International Application No. PCT/US2012/068744, International Preliminary Report on Patentability, Jul. 17, 2014, 11 pgs.
International Application Serial No. PCT/US2011/026349, Invitation to Pay Additional Fees mailed Jun. 9, 2011, 5 pgs.
International Application Serial No. PCT/US2012/068744, International Search Report mailed Apr. 25, 2013, 7 pgs.
International Application Serial No. PCT/US2012/068744, Written Opinion mailed Apr. 25, 2013, 9 pgs.
"JuggerKnot™ Soft Anchor. Labral Repair", brochure. Biomet Sports Medicine, (Apr. 2011), 12 pgs.
"Make your next tendon repair an open-and-shut case. The Teno Fix@ Tendon Repair System", Teno Fix@ brochure, Ortheon® Medical, (2003), 2 pgs.
"PANALOK Anchor with PDS II and ETHIBOND Suture", Mitek Products ETHICON, (1997), 2 pgs.
"Rotator Cuff Fixation", Acufex Fastenator System: Shoulder Arthroscopy, H-2-H-22.
"SE Graft Tensioning System Surgical Technique", Linvatec Corporation copyright 2003, (2004), 12 pgs.
"The AutoCuff System", Opus Medical, [Online]. Retrieved from the Internet: <www.opusmedical.com>, (2003), 4 pgs.
"Toggleloc™ Femoral Fixation Device", Arthrotek, (Mar. 31, 2006), 8 pgs.
Arthrotek, "A Biomet Company; Sure fire Hybrid Meniscal Device", Fall AANA, (2004), 37 pgs.
Barber, Alan F, "Uses and Abuses of Sutures and Anchors", Shoulder Scope, San Diego Shoulder Arthroscopy Library, (Jul. 1999), 6 pgs.

(56) References Cited

OTHER PUBLICATIONS

Barber, Alan F, "Using Sutures and Anchors", San Diego Shoulder Arthroscopy Course, 17th Annual Meetina, (Jun. 14, 2000), 9 pgs.

Charlton, Timothy M. D, "Ziptight Fixation System featuring Ziploop Technology", Ankle Syndesmosis Surgical Protocol Biomet Sports Medicine, (2009), 8 pgs.

Fahl, Tarek, "Toggleloc Fixation Device, MCL Reconstruction Surgical Protocol", Biomet Sports Medicine, (2011), 12 pgs.

Flavia, Namie Azato, "Traction endurance biomechanical study of metallic suture anchors at different insertion angles", Acta Ortop. Bras., vol. 11, No. 1, Sao Paulo, (Jan./Mar. 2003), pp. 25-31.

Fromm, Stuart M.D. E, "", Rapidloc, Meniscal Repair System, Mitek Products, Ethicon, (2001), 6 pgs.

Hecker, AT, et al., "Pull-out strength of suture anchors for rotator cuff and Bankart lesion repairs", The American Journal of Sports Medicine 21(6), (1993), 874-879.

Hunt, Patrick, et al., "Development of a Perforated Biodegradable Interference Screw; Arthroscopy:", The Journal of Arthroscopic and Related Surgery, vol. 21, No. 3;, (Mar. 2005), 258-265.

Kolter, Bill, "Biomet Sports Medicine's Juggerknot Soft Anchor Receives Gold Medical Design Excellence Award", (May 4, 2011), 2 pgs.

Lawhorn, M D, et al., "MaxFire™ Meniscal Repair Device with Zip Loop™ Technology", Biomet Sports Medicine, (Feb. 29, 2008), 12 pgs.

Majors, MD, Roy Alan, "Meniscal repairs: proven techniques and current trends", Lippincott Williams & Wilkins, Inc.;, (2002), 30-36.

Miller, Mark D, et al., "Pitfalls Associated with FasT-Fix Meniscal Repair", Arthroscopy: The Journal of Arthroscopic and Related Surgery, vol. 18 No. 8:, (Oct. 2002), 939-943.

Smith, et al., "Endoscopic Meniscal Repair Using the T-Fix", (1996), 16 pgs.

Smith, et al., "Fast-Fix", Meniscal Repair System;, (2001), 3 pgs.

Thomas, Roseberg D, "Technique for ACL Reconstruction with Acufex Director Drill Guide and Endobutton CL", Smith & Nephew, Technique Guide, (1999), 18 pgs.

Weiler, A, et al., "Biodegradierbare Interferenzschrauben in der Kreuzbandchirurgie", OPJOURNAL 14, (1998), 278-284.

US 6,238,418, 05/2001, Schwartz (withdrawn)

\* cited by examiner

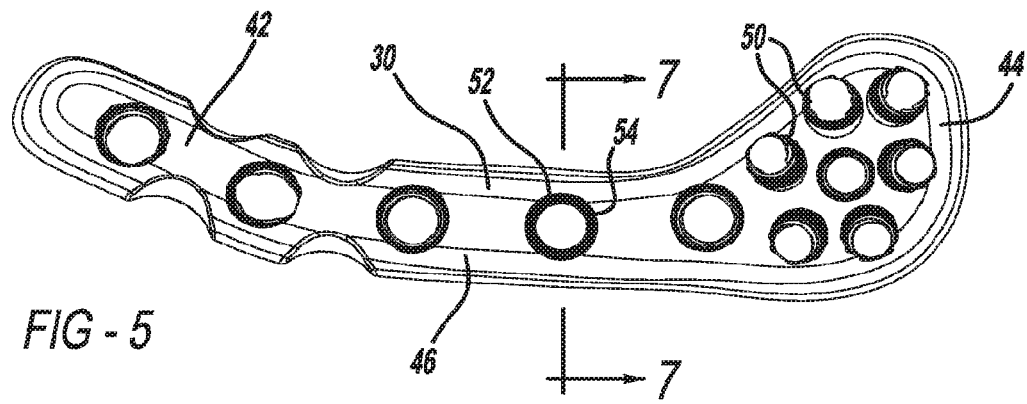
FIG - 5
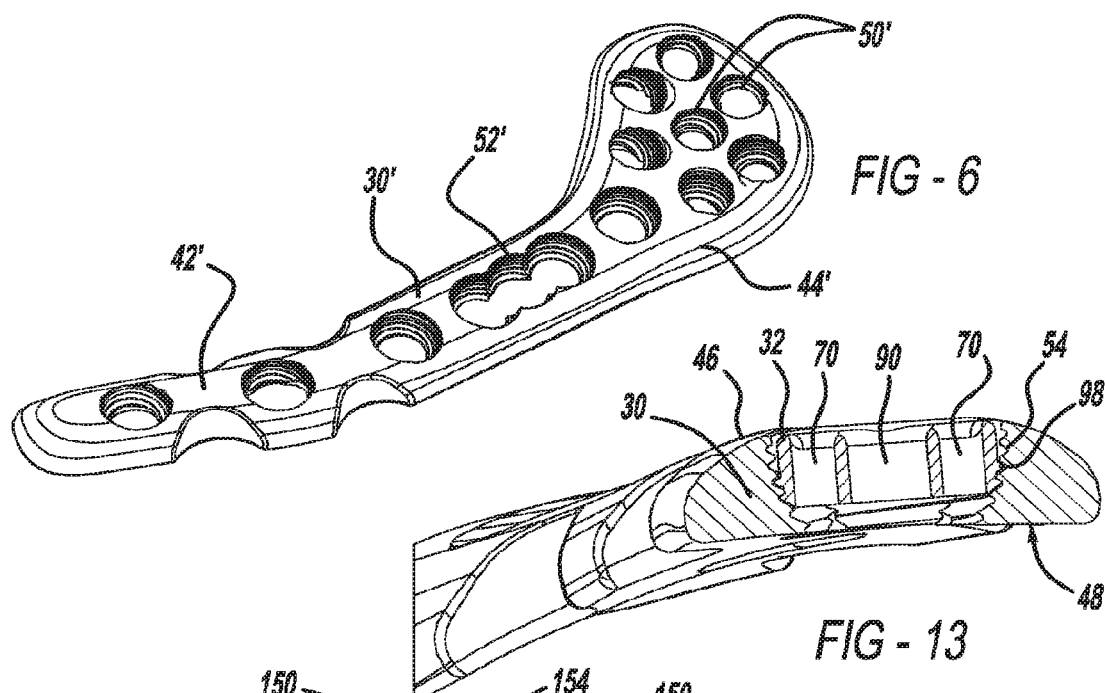
FIG - 6
FIG - 13
FIG - 14

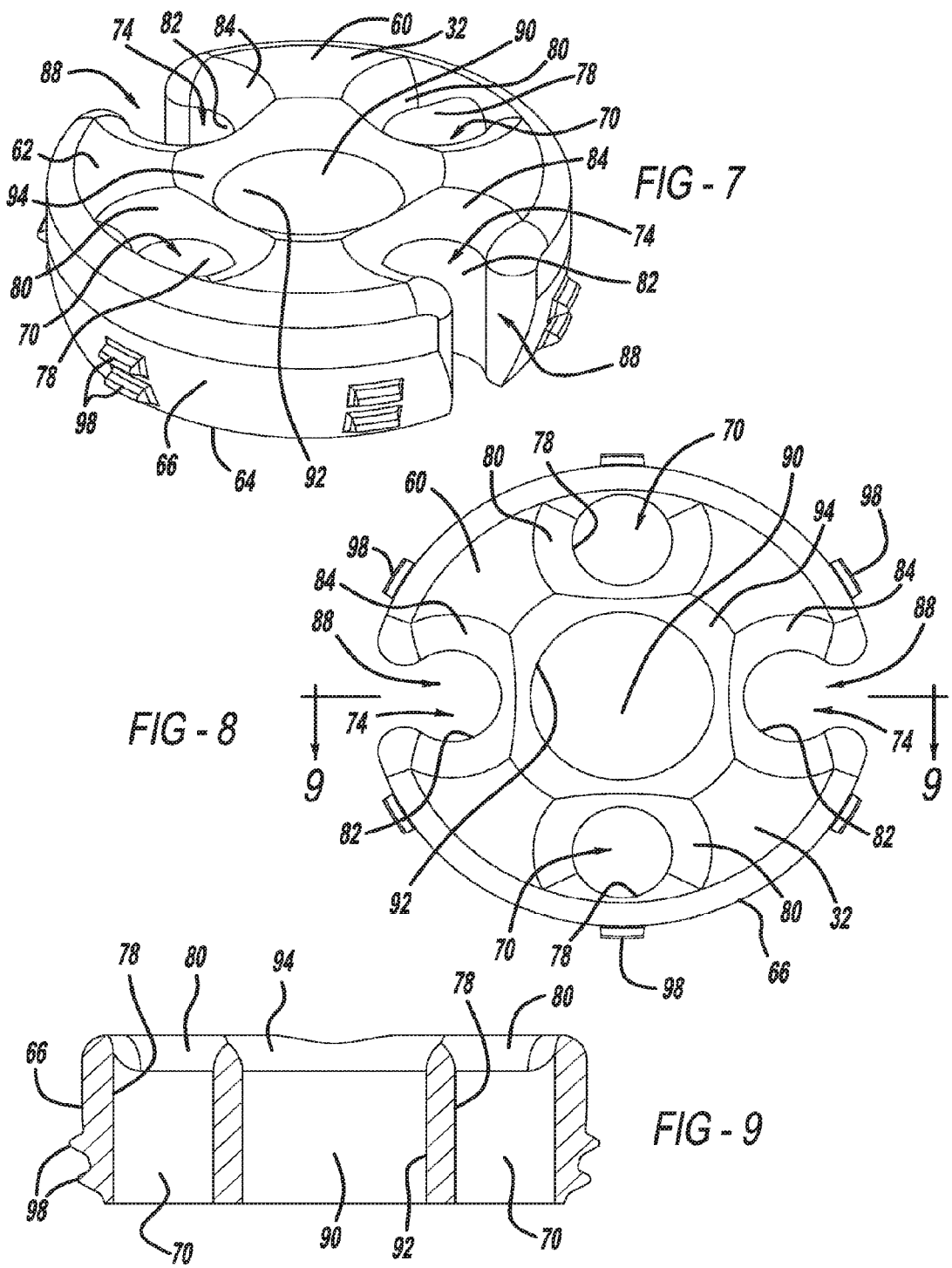

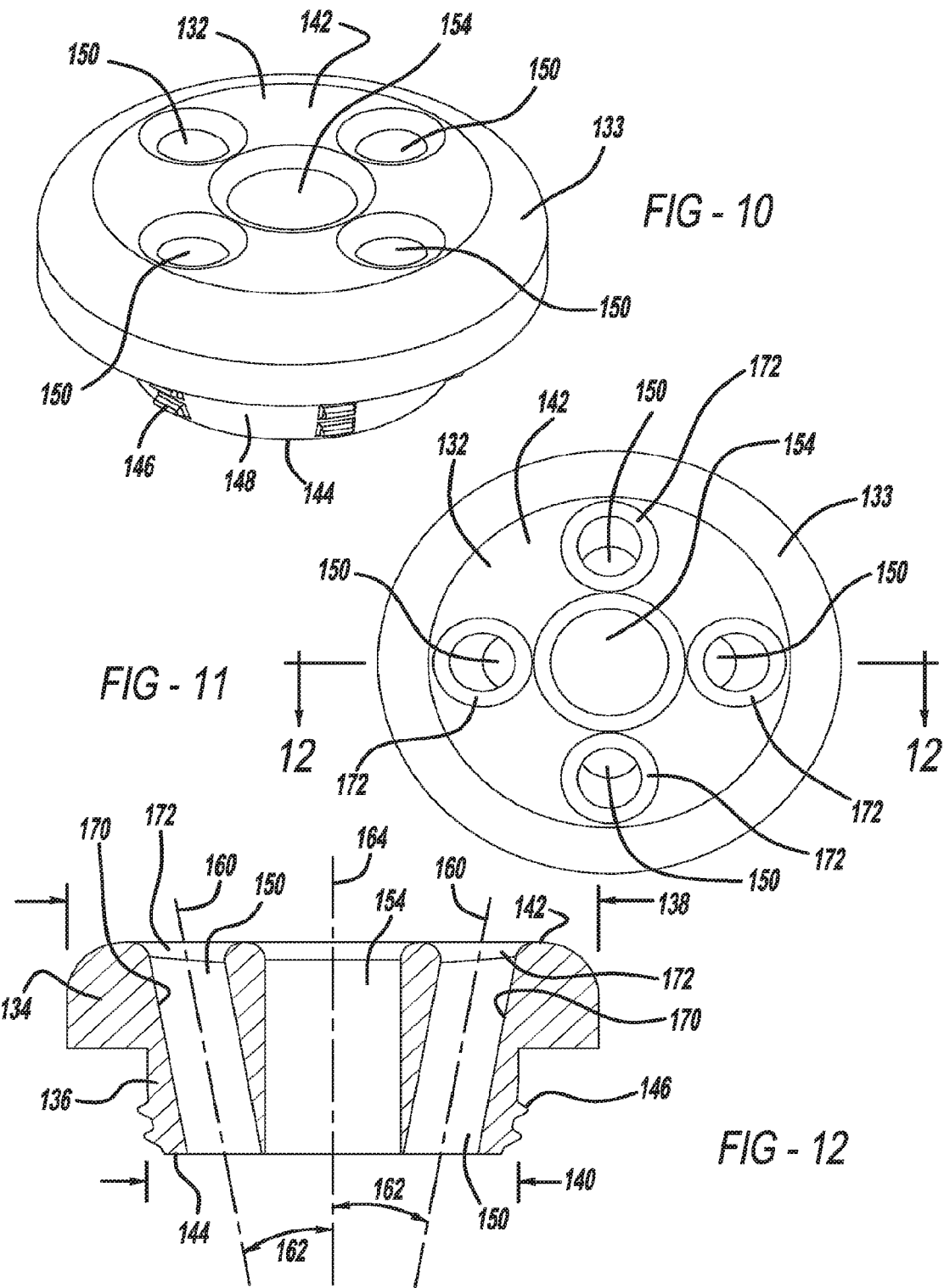

METHOD OF IMPLANTING A BONE FIXATION ASSEMBLY

CLAIM OF PRIORITY

This application is a divisional of U.S. patent application Ser. No. 13/342,646, filed on Jan. 3, 2012, the benefit of priority of which is claimed hereby, and which is incorporated by reference herein in its entirety.

FIELD

The present disclosure relates generally to bone fixation and more particularly, to a clavicle fixation assembly including a suture button, a bone plate, and a suture assembly that are used in combination to position a clavicle at a desired location relative to a scapula.

BACKGROUND

This section provides background information related to the present disclosure which is not necessarily prior art.

Portions of the anatomy can generally be formed relative to one another to allow for a natural articulation, support, movement, or the like. Nevertheless, due to various circumstances, such as injury, disease, or the like, various portions of the anatomy can become damaged. For example, a bone portion and/or surrounding tissue may become damaged in a manner that is substantially unnatural. It may be selected to perform a procedure relative to the bone portion to recreate the more natural bone portion.

For example, in some instances, a clavicle can become partially or completely fractured causing the clavicle, in some instances, to become misaligned relative to the surrounding anatomy including a coracoid process of a scapula. In some instances, coracoclavicular ligaments that connect between the clavicle and coracoid process can tear, causing a clavicle to unfavorably displace superiorly. In some circumstances, it may be difficult to properly locate the clavicle relative to a scapula.

SUMMARY

This section provides a general summary of the disclosure, and is not a comprehensive disclosure of its full scope or all of its features.

A bone fixation assembly can include a suture button, a bone plate, and a suture assembly. The suture button can include a body that has a first end surface, a second end surface, and a circumferential outer surface. A first pair of passages can be formed through the body from the first end surface to the second end surface. The circumferential outer surface can include at least one protrusion or retaining rib extending radially therefrom. The bone plate defines an aperture. The suture button is configured to be at least partially received into the aperture in an assembled position such that the retaining rib engages the bone plate and inhibits withdrawal of the suture button from the aperture in the assembled position. The suture assembly includes a suture engaging member and a suture configured to couple the suture engaging member in the suture button.

According to additional features, the suture button can further define a second pair of passages formed through the body from the first end surface to the second end surface. The body can also define a pair of radial openings that connect the second pair of passages, respectively with the circumferential outer surface. The suture button can further define a central passage. The first and second pair of passages can be located radially outwardly on the body relative to the central passage.

According to other features, the button can have a body that has an upper portion having a first diameter and a lower portion having a second diameter. The first diameter can be larger than the second diameter. The retaining rib can be formed on the lower portion. In one example, the first pair of passages taper toward each other from the first end surface to the second end surface. The lower portion can be configured to be received at least partially into the aperture of the bone plate and the upper portion can be configured to extend proud from the bone plate in the assembled position.

According to some examples, each passage of the first pair of passages is further defined by a chamfer surface that connects the first end surface with a radial sidewall. The aperture in the bone plate can be threaded such that the retaining rib positively engages the threads in the assembled position. The suture engaging member can comprise an elongated member having a passage formed therethrough. The suture can be configured to be looped through the passage in the suture engaging member. The elongated member can be configured to engage a bone in the assembled position such that the elongated member is inhibited from moving toward the suture button. In other examples, the elongated member can comprise a flexible tube that defines the passage. The flexible tube can be configured to expand and engage the bone in the assembled position.

A method of implanting a bone fixation assembly includes preparing a first hole through a clavicle. A second hole can be prepared through a coracoid process. A bone plate having an aperture can be positioned against the clavicle. A portion of suture can be located through the aperture, the first hole, and the second hole until a retaining member slidably disposed on the portion of suture locates against an outer surface of the coracoid process. A second portion of the suture can be passed through an aperture defined in the suture button. The suture button can be positively located into the bone plate aperture. The second portion of suture can be drawn away from the outer surface of the coracoid process causing tension between the retaining member and the bone plate. The second portion of the suture can be secured at a position that maintains the tension.

In some examples, positively locating the suture button includes engaging retaining ribs formed on a circumferential surface of the suture button with threads formed in the bone plate at the aperture. Drawing the second portion of the suture away from the outer surface of the coracoid process can include manipulating the retaining member from a first position that has an outer profile generally suitable to pass through the first and second holes to a second position that has an outer profile generally unsuitable to pass through the first and second holes.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

FIG. 5 is a plan view of an exemplary bone plate of the bone fixation assembly;

FIG. 6 is a perspective view of a bone plate constructed in accordance with additional features of the present teachings;

FIG. 7 is a front perspective view of a suture button constructed in accordance to one example of the present teachings;

FIG. 8 is a plan view of the suture button of FIG. 7;

FIG. 9 is a cross-sectional view of the suture button taken along line 9-9 of FIG. 8;

FIG. 10 is a perspective view of another suture button constructed in accordance to other features of the present teachings;

FIG. 11 is a plan view of the suture button of FIG. 10;

FIG. 12 is a cross-sectional view of the suture button taken along lines 12-12 of FIG. 11;

FIG. 13 is a cross-sectional view of the suture button shown in FIG. 7 in an assembled position relative to the bone plate of FIG. 5;

FIG. 14 is a cross-sectional view of the suture button of FIG. 10 shown in an assembled position relative to the bone plate of FIG. 5;

Corresponding reference numerals indicate corresponding parts throughout the several views of the drawings.

DETAILED DESCRIPTION

Example embodiments will now be described more fully with reference to the accompanying drawings.

The following description of the various embodiments is merely exemplary in nature and is in no way intended to limit the teachings, their application or uses. While the following description is directed toward an apparatus and method for fixing a right clavicle relative to a coracoid process of a scapula and other surrounding anatomy of a patient, it would be appreciated that the same may be applied to fixation of a left clavicle. In this regard, the apparatus disclosed herein may be used in other implants including those that incorporate a bone plate. For example, the apparatus disclosed herein may be incorporated in a periprosthetic situation where using a bone screw may be insufficient or unfavorable such as when a far cortex may not adequately support the threads of the bone screw.

Figure 1:
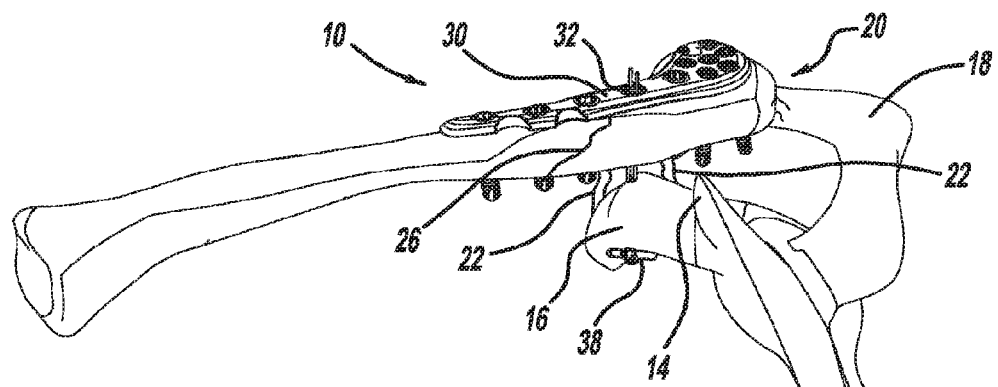
FIG. 1 is a posterior perspective view of a bone fixation assembly constructed in accordance to one example of the present teachings and shown in an implanted position relative to a right clavicle and scapula of a patient.
Figure 3:
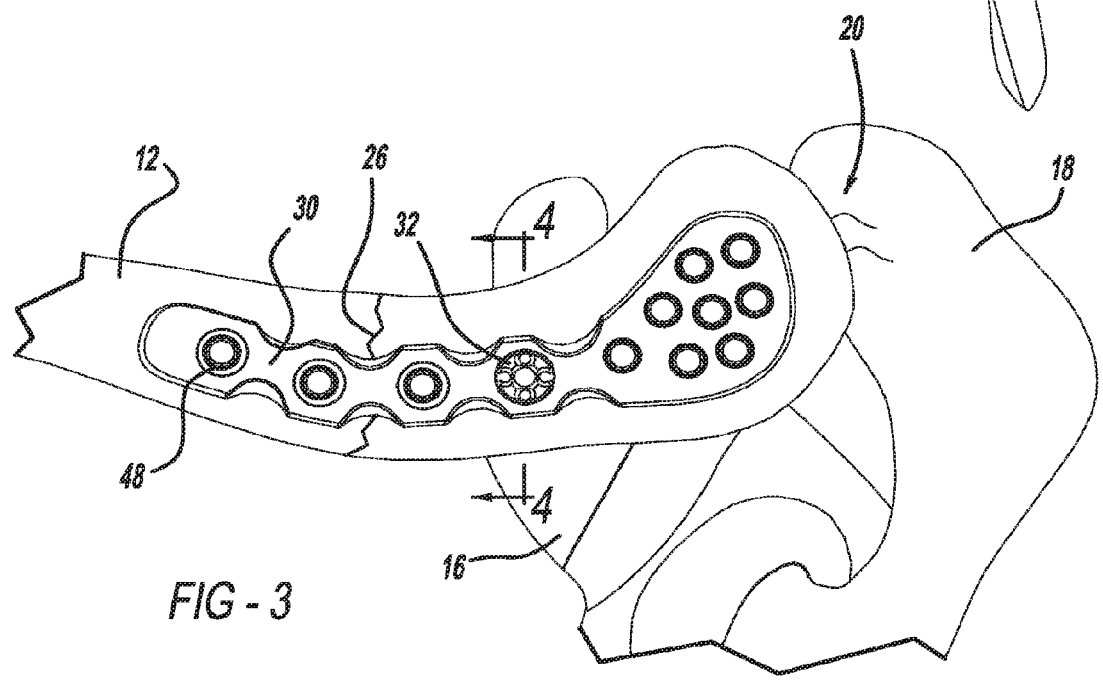
FIG. 3 is a superior plan view of the bone fixation assembly of FIG. 1.
Figure 2:
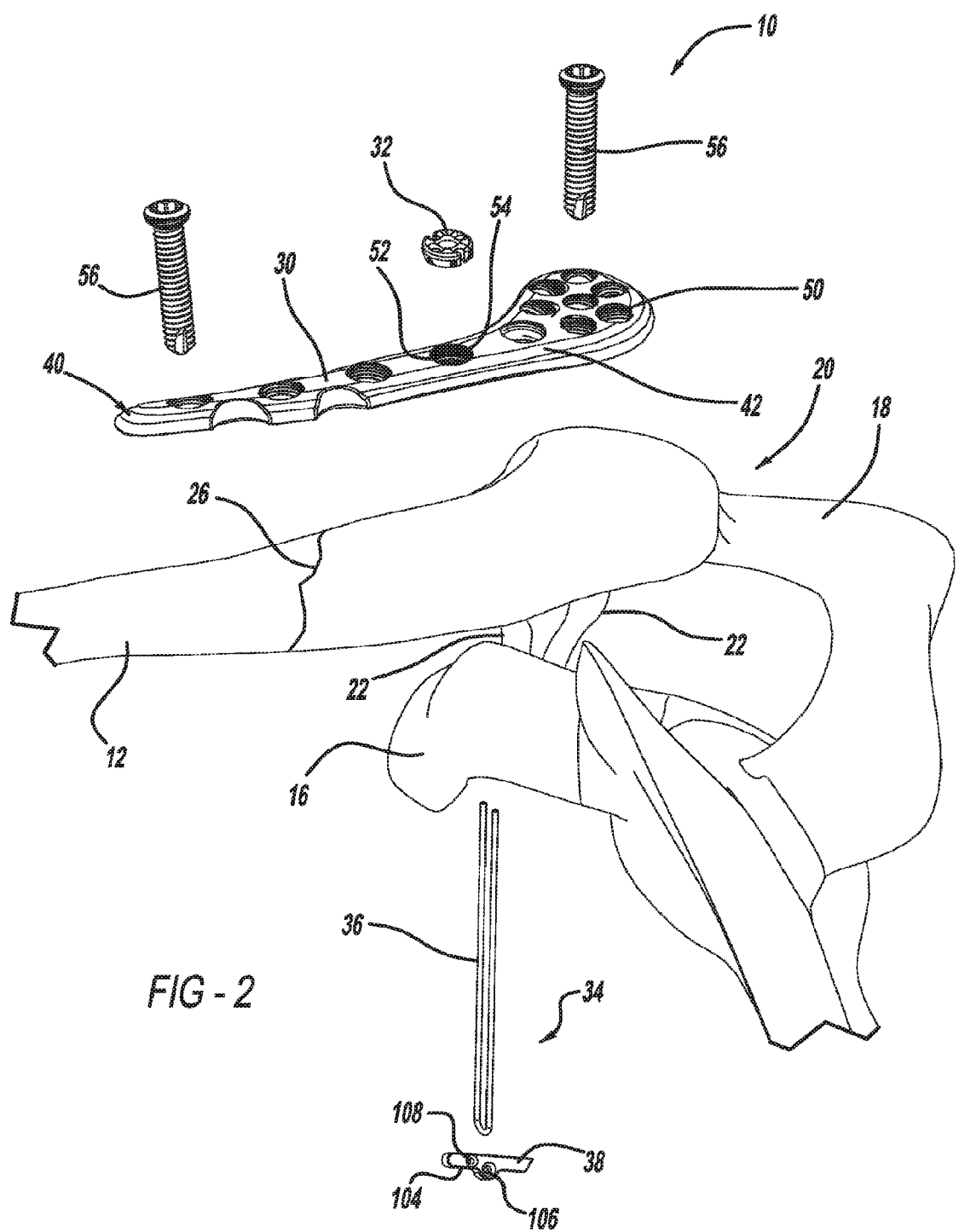
FIG. 2 is an exploded perspective view of the bone fixation assembly of FIG. 1 and shown relative to a clavicle, coracoid process, and acromion.

With initial reference to FIGS. 1-3, a bone fixation assembly constructed in accordance with one example of the present teachings is shown and generally identified at reference numeral 10. The bone fixation assembly 10 is shown in an implanted position in FIGS. 1 and 3. Briefly, a patient's anatomy can include a clavicle 12 and a scapula 14 having a coracoid process 16 and acromion 18. The clavicle 12 and acromion 18 can cooperate to form an articulating portion such as the acromioclavicular joint 20. Various ligaments can connect the clavicle 12 with portions of the scapula 14 such as coracoclavicular ligaments 22 (FIG. 2) that are connected between the clavicle 12 and the coracoid process 16. The clavicle 12 is illustrated having a fracture 26. Additionally, or alternatively, the coracoclavicular ligaments 22 can be torn. Such conditions can unfavorably cause the clavicle 12 to move generally superiorly and posteriorly relative to the coracoid process 16. As will become appreciated from the following description, the bone fixation assembly 10 according to the present teachings, once implanted, can generally fix the clavicle 12 back to a desired position such that the unfavorable superior/posterior deflection of the clavicle can be reduced as well as re-approximate fractured clavicle 12 for healing.

Figure 4:
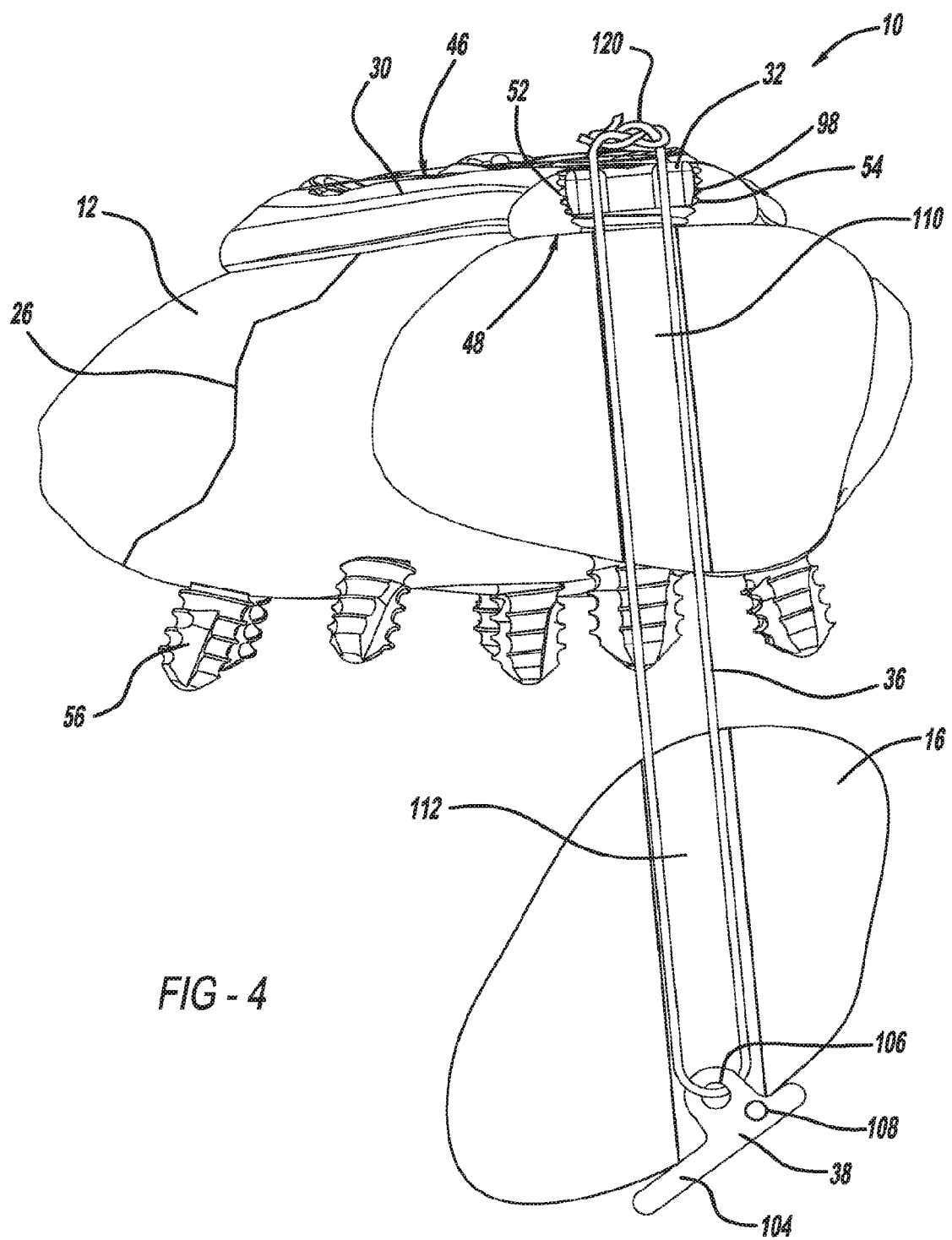
FIG. 4 is a cross-sectional view of the bone fixation assembly taken along line 4-4 of FIG. 3.

With continued reference to FIGS. 1-3 and additional reference to FIGS. 4 and 5, the bone fixation assembly 10 will be further described. The bone fixation assembly 10 can generally include a bone plate 30, a suture button 32, and a suture assembly 34 including a suture 36 and a suture engaging member 38. The bone plate 30 can generally include an elongated plate body 42 having a sloped circumferential surface 44. The elongated plate body 42 can further include an outer surface 46 and an opposite bone engaging surface 48 (FIG. 4). A plurality of threaded apertures 50 can be formed through the bone plate 30 from the outer surface 46 to the bone engaging surface 48. A threaded aperture 52 can be located generally centrally on the bone plate 30. The threaded aperture 52 can be formed similar to the threaded apertures 50. In this regard, the threaded aperture 52 includes threads 54 formed thereon. It will be appreciated that the shape and configuration of the bone plate 30 is merely exemplary and that other bone plates may be used within the scope of the present teachings. Bone screws 56 may be threaded into the threaded apertures 50 as needed to engage bone and/or tissue beyond the bone engaging surface 48 of the bone plate 30. In some examples, the bone plate 30 may additionally or alternatively incorporate non-threaded holes and/or slots that can each cooperatively receive a suture button 32 (or other suture buttons having different configurations).

Referencing now FIG. 6, a bone plate 30' constructed in accordance to additional features of the present teachings is shown. The bone plate 30' can include similar features as the bone plate 30 described above. In this regard, the bone plate 30' can include an elongated plate body 42' having threaded apertures 50'. A threaded aperture 52' located generally in the center of the bone plate 30' can collectively define multiple overlapping threaded apertures. In this regard, the threaded aperture 52' can provide the surgeon with additional versatility for locating a suture button 32 during implantation.

With particular reference now to FIGS. 7-9, the suture button 32 will be described in greater detail. The suture button 32 generally comprises a body 60 that includes a first end surface 62, a second end surface 64, and a circumferential outer surface 66. A first pair of passages 70 are formed through the body 60 from the first end surface 62 to the second end surface 64. A second pair of apertures 74 are formed through the body 60 from the first end surface 62 to the second end surface 64. The first pair of passages 70 are generally defined by a first pair of radial sidewalls 78 and a corresponding pair of chamfer surfaces 80 that connect the radial sidewall 78 with the first end surface 62. Similarly, the second pair of apertures 74 can be generally defined by a corresponding pair of radial sidewalls 82 and a pair of chamfer surfaces 84 that generally connect the radial sidewalls 82 with the first end surface 62. The body 60 can generally define a pair of radial openings 88 that are formed through the circumferential outer surface 66 and connect with the second pair of apertures 74. As will become appreciated, the first and second pair of passages 70 and 74 can be configured to accept the suture 36 therethrough when securing the suture assembly 34 to the suture button 32. The radial openings 88 can offer a surgeon radial access for the suture 36 to the second pair of apertures 74.

A central passage 90 is formed through the body from the first end surface 62 to the second end surface 64. The central passage 90 can generally be defined by a central radial sidewall 92 and a corresponding central chamfer surface 94. A plurality of radial protrusions or retaining ribs 98 extend from the circumferential outer surface 66. In the example shown, six pair of discontinuous and equally spaced retaining ribs 98 are positioned around the circumferential outer surface 66. As will be described herein, the retaining ribs 98 can be configured to positively locate and engage the threads 54 formed on the bone plate 30 in an assembled position. It will be appreciated that in other configurations the retaining ribs 98 can engage other features incorporated on the bone plate 30 such as a groove or chamfer. It other examples, the suture button 32 may be configured without the retaining ribs 98.

Returning now to FIG. 2, the suture assembly 34 will now be described according to one example. The suture engaging member 38 illustrated in FIG. 2 can generally define an elongated body 104 having a first eyelet 106 and a second eyelet 108. In general, the suture engaging member 38 can have a profile that can be advanced through a first bone hole 110 prepared in the clavicle 12 and a second bone hole 112 prepared in the coracoid process 16. In the particular example shown, the suture engaging member 38 is in the form of a ToggleLoc™ offered by Biomet Sports Medicine, LLC of Warsaw, Ind. Additional features and description of the ToggleLoc™ may be found in commonly owned U.S. Pat. No. 7,500,983, which is expressly incorporated herein by reference. Other retaining members may be additionally or alternatively used to locate the suture 36 relative to the coracoid process 16.

With particular reference now to FIG. 4, one example of implanting the bone fixation assembly 10 according to the present teachings will be described. Initially, the preferred orientation and location of the bone plate 30 will be assessed by the surgeon. Similarly, a properly sized component of the bone fixation assembly 10 for the particular patient and injury to be treated can be selected.

The first bone hole 110 can then be prepared through the clavicle 12. The second bone hole 112 can then be prepared through the coracoid process 16. The bone plate 30 can then the positioned against the clavicle 12 such that the bone engaging surface 48 engages the clavicle 12. The suture engaging member can then be advanced through the first and second bone holes 110 and 112 and rotated generally into the position illustrated in FIG. 4 where the elongated body 104 can generally engage an outer surface of the coracoid process 16 and fix a first portion of suture 36. A second portion of the suture 36 can then be located through any combination of the first and second pairs of passages 70 and 74 of the suture button 32.

The suture button 32 can be advanced at least partially into the threaded aperture 52 until the retaining ribs 98 engage the threads 54 or other feature on the bone plate 30. It is contemplated that the retaining ribs 98 can achieve a snap fit or otherwise attain a fixed relationship relative to the bone plate 30. The suture 36 can then be tied as illustrated at reference number 120. It is contemplated that the sequence of steps may be altered as needed. For example, a surgeon may advance the suture button 32 into the threaded aperture 52 concurrently while tying the knot 120. The arrangement of the bone fixation assembly 10 of the present teachings provides a surgeon the ability to capture and fix a length of clavicle 12 that may have a fracture 26 while concurrently offering a tension and retaining force between the clavicle 12 and the coracoid process 16 with one fixation assembly. Such an arrangement can also be particularly advantageous when addressing a clavicle 12 that has torn or damaged coracoclavicular ligaments 22. It is contemplated that the bone fixation assembly 10 may be offered in a pre-packaged kit.

With reference now to FIGS. 10-12, a suture button 132 constructed in accordance to additional features of the present teachings will be described. The suture button 132 can include similar features as discussed above with respect to the suture button 32. The suture button 132 can have a body 133 that includes an upper portion 134 and a lower portion 136 (see FIG. 12). The upper portion 134 can have an upper diameter 138 while the lower portion 136 can have a lower diameter 140. The upper diameter 138 can be greater than the lower diameter 140 such that the upper portion 134 can sit proud relative to an outer surface 46 of the bone plate (see FIG. 14). The body 133 can generally include a first end surface 142 and a second end surface 144. Radial protrusions or retaining ribs 146 can be formed around a circumferential surface 148 of the lower portion 136.

Two pairs of passages 150 can be formed through the body 133 from the first end surface 142 to the second end surface 144. A central passage 154 can be formed through the body 133 from the first end surface 142 to the second end surface 144. Each passage 150 can have an axis 160 that defines an angle 162 relative to an axis 164 of the central passage 154. The passages 150 are defined by a pair of radial sidewalls 170 (FIG. 12) and a corresponding pair of chamfer surfaces 172 (FIG. 11) that connect the radial sidewall 152 with the first end surface 142. The passages 150 generally taper inwardly from the first end surface 142 to the second end surface 144. Such a configuration can offer a surgeon more space to manipulate suture extending from the passages 150 as well as maneuver a rod 180 of a insertion tool 182 (as is described herein with respect to FIGS. 15-17).

Figure 15:
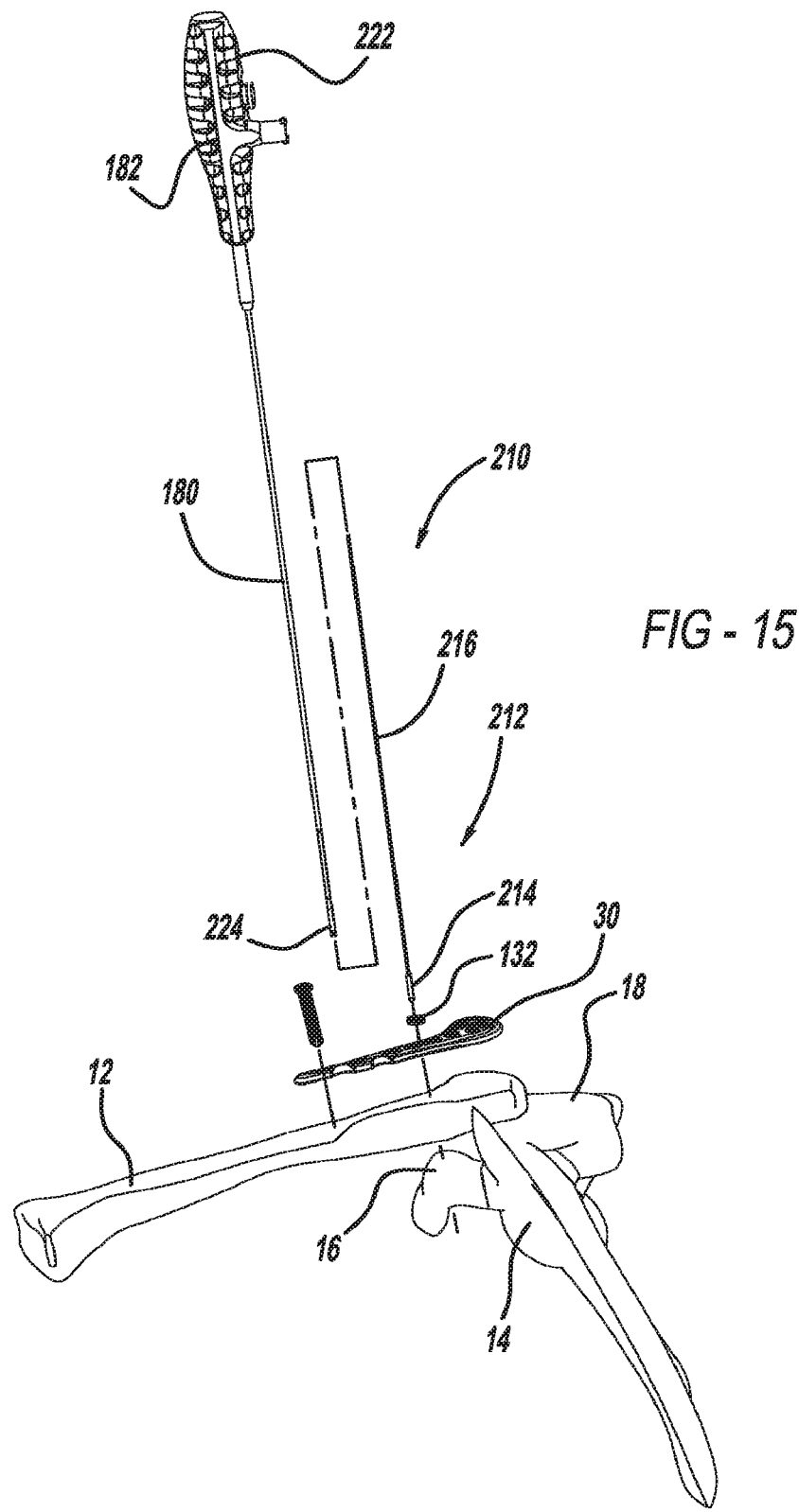
FIG. 15 is an exploded view of a bone fixation assembly constructed in accordance to another example of the present teachings that incorporates the suture button of FIG. 11 and an alternate suture engaging member.
Figure 16:
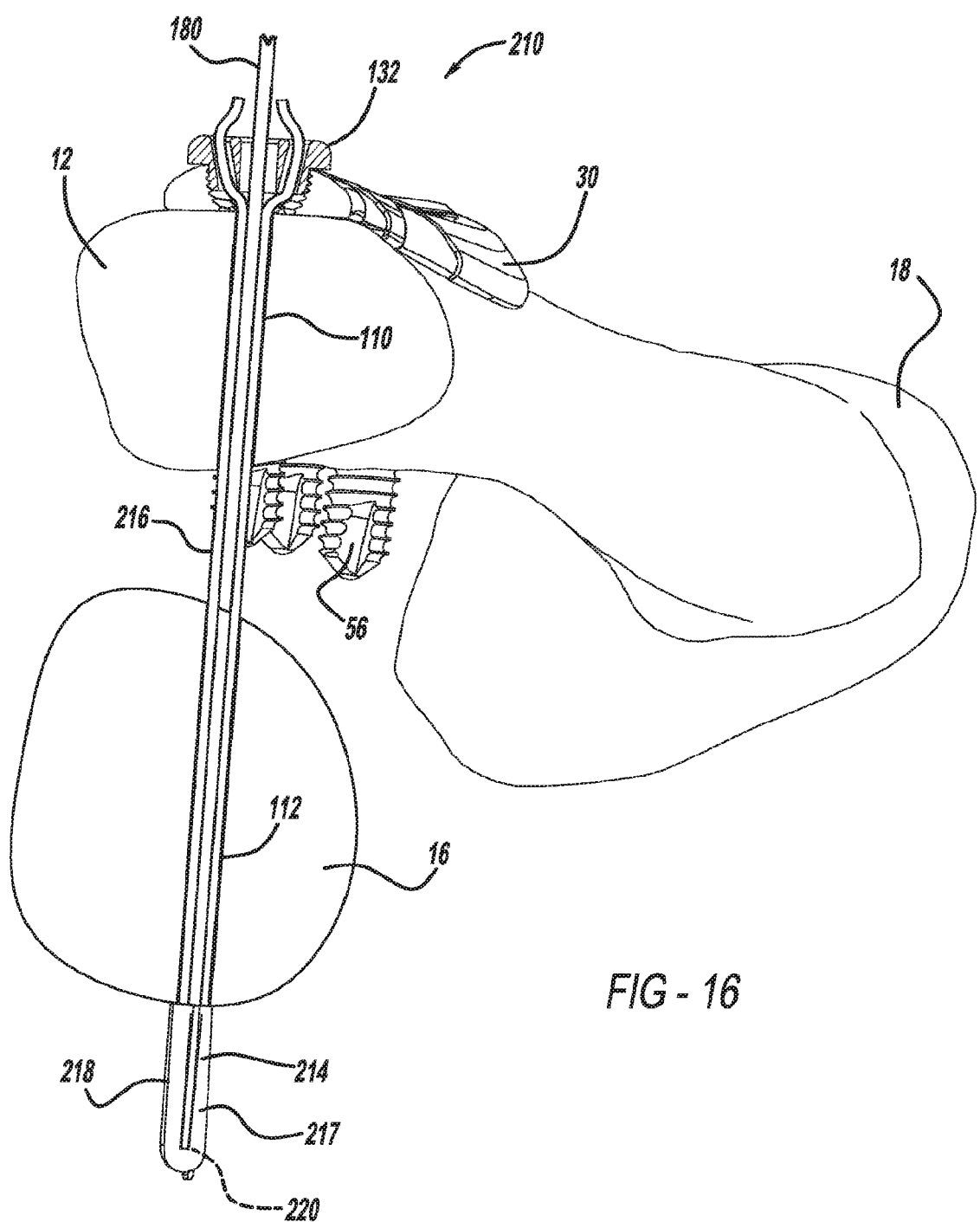
FIG. 16 is a cross-sectional view of the bone fixation assembly of FIG. 15 and shown with an insertion tool passing the elongated member through a first hole in the clavicle and a second hole through the coracoid process during an implantation step.
Figure 17:
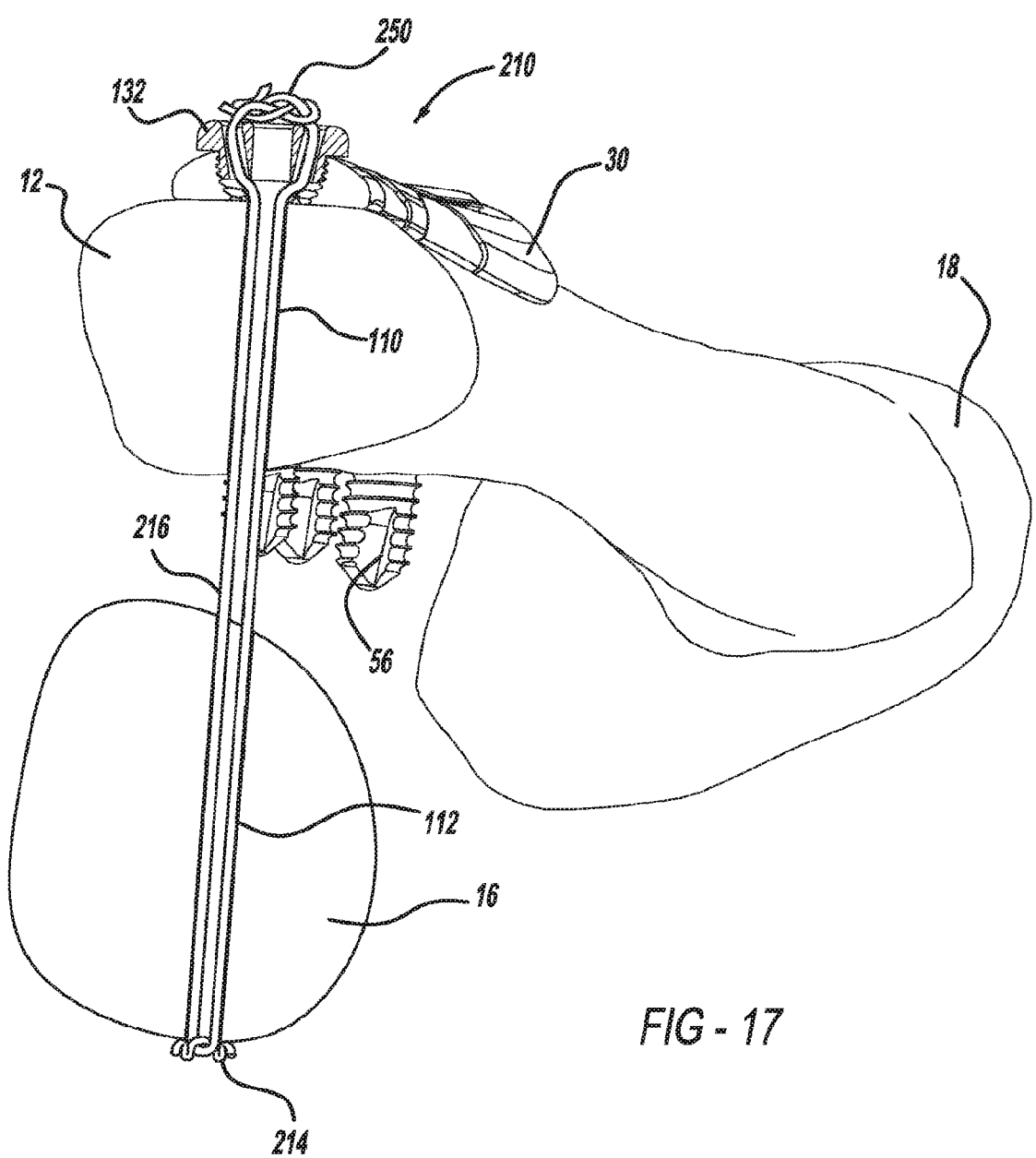
FIG. 17 is a cross-sectional view of the bone fixation assembly shown in FIG. 16 and shown with the insertion tool removed and the suture tied in an implanted position.

Turning now to FIGS. 15-17, a bone fixation assembly 210 constructed in accordance to additional features of the present teachings will be described. The bone fixation assembly 210 generally includes the bone plate 30, the suture button 132, and a suture assembly 212 that includes a suture engaging member 214 and a suture 216. It is appreciated that while the bone fixation assembly 210 is described herein as being associated with the suture button 132, the suture button 32 can be also used. Similarly, while the suture engaging member 214 will be described as associated with the embodiment of FIGS. 15-17, the suture engaging member 38 can alternatively be used. The suture engaging member 214 can generally include an elongated member 217 having a flexible tube 218 that defines a passage 220 therethrough. In one example, the suture engaging member 214 can include a JuggerKnot™ Soft Anchor offered by Biomet Sports Medicine, LLC of Warsaw, Ind.

The insertion tool 182 can generally include a handle 222 that is connected to the rod 180. During use, once a first bone hole 110 has been prepared in the clavicle 12 and the second bone hole 112 has been prepared in the coracoid process 16, a distal end 224 of the rod 180 can be used to pass the suture engaging member 214 with a portion of suture 216 through the first bone hole 110 of the clavicle 12 and the second bone hole 112 of the coracoid process 16 until the suture engaging member 214 extends out of the second bone hole 112 of the coracoid process 16 (FIG. 16). Next, the insertion tool 182 can be withdrawn from the coracoid process 16 and the clavicle 12. A second portion of the suture 216 can be located as desired through respective passages 150 in the suture button 132. The suture 216 then can be pulled causing the flexible tube 218 of the suture engaging member 214 to generally expand to a position shown in FIG. 17 and inhibit the suture 216 from being withdrawn through the second bone hole 112 of the coracoid process 16. The suture 216 can then be tied at reference numeral 250 as shown in FIG. 17. The suture button 132 can then be advanced at least partially into the threaded aperture 52 causing the retaining ribs 146 to positively lock with the threads 54 of the threaded aperture 52. Again, it will be appreciated that the sequence of steps are exemplary and may be altered as needed. It will be appreciated that the desired amount of tension can be applied to the suture 216 causing the clavicle 12 to be moved to a desired orientation.

Figure 18:
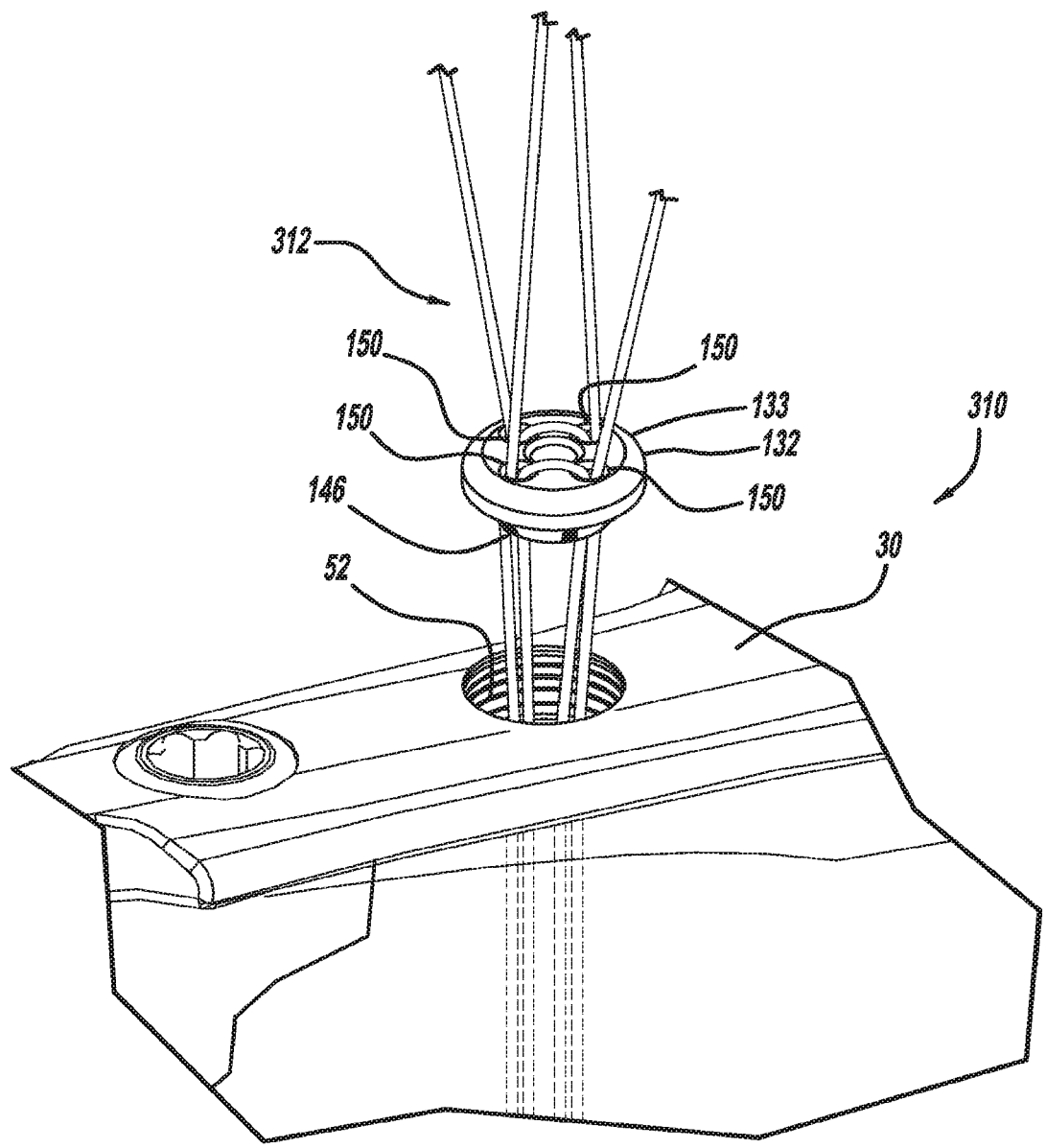
FIG. 18 is an exploded perspective view of a bone fixation assembly that incorporates a suture configuration according to additional features.

Turning now to FIG. 18, a bone fixation assembly 310 constructed in accordance to additional features of the present teachings will be described. The bone fixation assembly 310 generally includes the bone plate 30, the suture button 132, and a suture assembly 312. The suture assembly 312 can include a ZipLoop™ suture configuration offered by Biomet Sports Medicine, LLC of Warsaw, Ind. The ZipLoop™ may be threaded for use with the passages 150 formed through the body 133 of the suture button 132. The suture assembly 312 may cooperate with a suture engaging member such as the suture engaging member 38 shown in FIG. 4 (FIG. 4) described above. Additional description of the ZipLoop™ and its operation may be found in commonly owned U.S. Pat. No. 7,658,751, issued on Feb. 9, 2010; U.S. Pat. No. 7,601,165, issued on Oct. 13, 2009; and pending U.S. application Ser. No. 12/719,337, filed on Mar. 18, 2010, which are all expressly incorporated herein by reference.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A method of implanting a bone fixation assembly, the method comprising:
   positioning a portion of a suture through an eyelet in a suture engaging member to form first and second suture strands extending from opposite sides of the eyelet, the suture engaging member being elongated along a longitudinal direction;
   advancing the suture engaging member in a longitudinal orientation through a bone plate aperture in a bone plate, through a clavicle hole in a clavicle, and through a coracoid process hole in a coracoid process, so that the first and second suture strands extend from the eyelet sequentially through the coracoid process hole, the clavicle hole, and the bone plate aperture;
   advancing a suture button over the first and second suture strands into the bone plate aperture;
   securing the suture button to the bone plate by engaging retaining ribs formed on a circumferential surface of the suture button with one or more threads formed in the bone plate at the bone plate aperture;
   pulling on the first and second suture strands to:
      pivot the suture engaging member away from the longitudinal orientation so that the suture engaging member has an outer profile unsuitable for entering the coracoid process hole, and
      produce tension between the suture engaging member and the bone plate; and
   tying the first and second suture strands together to maintain the tension.

2. The method of claim 1, wherein the first and second suture strands extend through respective first and second longitudinal passages in the suture button.

3. The method of claim 2, wherein the first and second passages are positioned on opposite sides of a longitudinal axis of the suture button.

4. The method of claim 3, wherein the first and second passages are radially accessible through a lateral edge of the suture button.

5. The method of claim 3, wherein the first and second passages are radially inaccessible through a lateral edge of the suture button.

6. The method of claim 1, wherein:
   the first and second suture strands extend through a single longitudinal passage in the suture button; and
   the first and second suture strands are tied together in a knot that is too large to fit in the single longitudinal passage.

7. The method of claim 1, wherein the retaining ribs are discontinuous around the circumference of the suture button.

8. The method of claim 1, wherein the retaining ribs are arranged in groups around the circumference of the suture button, the ribs in each group being longitudinally offset from one another.

9. The method of claim 1, further comprising positioning the bone plate proximate the clavicle.

10. The method of claim 1, further comprising:
    preparing the clavicle hole through the clavicle; and
    preparing the coracoid process hole through the coracoid process.

11. A method of implanting a bone fixation assembly, the method comprising:
    locating a portion of a suture through a bone plate aperture in a bone plate, through a clavicle hole in a clavicle, and through a coracoid process hole in a coracoid process, until a retaining member slidably disposed on the portion of the suture locates against an outer surface of the coracoid process;
    passing a second portion of the suture through a suture button aperture defined in a suture button;
    positively locating the suture button into the bone plate aperture including engaging retaining ribs formed on a circumferential surface of the suture button with one or more threads formed in the bone plate at the bone plate aperture;

drawing the second portion of the suture away from the outer surface of the coracoid process causing tension between the retaining member and the bone plate; and securing the second portion of the suture at a position that maintains the tension.

12. The method of claim 11, wherein drawing the second portion of the suture away from the outer surface of the coracoid process comprises:

manipulating the retaining member from a first position that has an outer profile generally suitable to pass through the clavicle hole and the coracoid process hole to a second position that has an outer profile generally unsuitable to pass through the coracoid process hole.

13. The method of claim 11, wherein drawing the second portion of the suture away from the outer surface of the coracoid process comprises:

manipulating the retaining member from a first position that has an outer profile generally suitable to pass through the clavicle hole and the coracoid process hole to a second position that has an outer profile generally unsuitable to pass through the clavicle hole and the coracoid process hole.

14. The method of claim 11, further comprising:
positioning the bone plate proximate the clavicle;
preparing the clavicle hole through the clavicle; and
preparing the coracoid process hole through the coracoid process.

15. The method of claim 11, wherein the retaining ribs are discontinuous around the circumference of the suture button.

16. The method of claim 11, wherein the retaining ribs are arranged in groups around the circumference of the suture button, the ribs in each group being longitudinally offset from one another.

17. A method of implanting a bone fixation assembly, the method comprising:

preparing a clavicle hole through a clavicle;

preparing a coracoid process hole through a coracoid process;

positioning a bone plate having an aperture proximate the clavicle;

locating a portion of a suture through the aperture, the clavicle hole, and the coracoid process hole, until a retaining member slidably disposed on the portion of the suture locates against an outer surface of the coracoid process;

passing a second portion of the suture through an aperture defined in a suture button;

positively locating the suture button into the bone plate aperture including engaging retaining ribs formed on a circumferential surface of the suture button with one or more threads formed in the bone plate at the aperture;

drawing the second portion of the suture away from the outer surface of the coracoid process causing tension between the retaining member and the bone plate; and securing the second portion of the suture at a position that maintains the tension.

18. The method of claim 17, wherein drawing the second portion of the suture away from the outer surface of the coracoid process comprises:

manipulating the retaining member from a first position that has an outer profile generally suitable to pass through the clavicle hole and the coracoid process hole to a second position that has an outer profile generally unsuitable to pass through the clavicle hole and the coracoid process hole.

19. The method of claim 17, wherein the retaining ribs are discontinuous around the circumference of the suture button.

20. The method of claim 17, wherein the retaining ribs are arranged in groups around the circumference of the suture button, the ribs in each group being longitudinally offset from one another.

* * * * *